US006983176B2

(12) United States Patent
Gardner et al.

(10) Patent No.: US 6,983,176 B2
(45) Date of Patent: Jan. 3, 2006

(54) OPTICALLY SIMILAR REFERENCE SAMPLES AND RELATED METHODS FOR MULTIVARIATE CALIBRATION MODELS USED IN OPTICAL SPECTROSCOPY

(75) Inventors: Craig Gardner, Brookline, MA (US); Michael J. Haass, Albuquerque, NM (US); Robert K. Rowe, Corrales, NM (US); Howland Jones, Edgewood, NM (US); Steven T. Strohl, Cedar Crest, NM (US); Matthew J. Novak, Tucson, AZ (US); Russell E. Abbink, Albuquerque, NM (US); David Nuñez, Sandia Park, NM (US); William Gruner, Edgewood, NM (US); Robert D. Johnson, Albuquerque, NM (US)

(73) Assignee: Rio Grande Medical Technologies, Inc., Albuquerque, NM (US)

(*) Notice: Subject to any disclaimer, the term of this patent is extended or adjusted under 35 U.S.C. 154(b) by 649 days.

(21) Appl. No.: 09/832,608

(22) Filed: Apr. 11, 2001

(65) Prior Publication Data

US 2003/0023170 A1 Jan. 30, 2003

(51) Int. Cl.
*A61B 5/00* (2006.01)

(52) U.S. Cl. .......................... 600/310; 600/473; 600/476
(58) Field of Classification Search ................ 600/310, 600/322, 323, 331, 473, 475, 476, 477; 356/39, 356/42, 432; 250/252.1, 339.09; 422/82.05, 422/82.09; 436/164, 171
See application file for complete search history.

(56) References Cited

U.S. PATENT DOCUMENTS 3,910,701 A 10/1975 Henderson et al.
4,035,083 A 7/1977 Woodriff et al.
(Continued)

FOREIGN PATENT DOCUMENTS

| EP | 0 426 358 B1 | 5/1991 |
|---|---|---|
| EP | 0 449 335 A2 | 10/1991 |

(Continued)

OTHER PUBLICATIONS

Anderson, Robert J. et al., "Errors in Absorbance Measurements in Infrared Fourier Transform Spectrometry because of Limited Instrument Resolution," *Analytical Chemistry*, vol. 47, No. 14, Dec., 1975, pp. 2339–2347.

(Continued)

*Primary Examiner*—Eric F. Winakur
(74) *Attorney, Agent, or Firm*—Crompton, Seager & Tufte, LLC

(57) ABSTRACT

Systems and methods for establishing and/or maintaining the prediction capability over time of a multivariate calibration model designed for quantitative optical spectroscopic measurement of attributes or analytes in bodily tissues, bodily fluids or other biological samples, which are particularly useful when the spectral absorbance of the attribute or analyte is small relative to the background. The present invention provides an optically similar reference sample to capture the characteristics of instrument and environmental variation and to reduce the effect of such variation on the measurement capability of the model. The optically similar reference is preferably stable over time and is designed such that its optical properties are sufficiently matched to the sample of interest that instrument and environmental variations are captured in the same manner in both the test sample of interest and the optically similar reference sample. The optically similar reference sample may include one or more physical components which are spectroscopically measured in a manner which closely mimics the spectroscopic measurement of the test sample of interest. Spectral similarity may also be achieved by using alternative components with spectral characteristics similar to the components contained in the test sample of interest.

86 Claims, 12 Drawing Sheets

U.S. PATENT DOCUMENTS

| | | |
|---|---|---|
| 4,142,797 A | 3/1979 | Astheimer |
| 4,169,676 A | 10/1979 | Kaiser |
| 4,260,220 A | 4/1981 | Whitehead |
| 4,427,889 A | 1/1984 | Muller |
| 4,537,484 A | 8/1985 | Fowler et al. |
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |
| 4,657,397 A | 4/1987 | Oehler et al. |
| 4,661,706 A | 4/1987 | Messerschmidt et al. |
| 4,684,255 A | 8/1987 | Ford |
| 4,712,912 A | 12/1987 | Messerschmidt |
| 4,730,882 A | 3/1988 | Messerschmidt |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,975,581 A | 12/1990 | Robinson et al. |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,068,536 A | 11/1991 | Rosenthal |
| 5,070,874 A | 12/1991 | Barnes et al. |
| 5,158,082 A | 10/1992 | Jones |
| 5,178,142 A | 1/1993 | Harjunmaa et al. |
| 5,179,951 A | 1/1993 | Knudson |
| 5,204,532 A | 4/1993 | Rosenthal |
| 5,222,496 A | 6/1993 | Clarke et al. |
| 5,223,715 A | 6/1993 | Taylor |
| 5,225,678 A | 7/1993 | Messerschmidt |
| 5,243,546 A | 9/1993 | Maggard |
| 5,257,086 A | 10/1993 | Fateley et al. |
| 5,267,152 A | 11/1993 | Yang et al. |
| 5,268,749 A | 12/1993 | Weber et al. |
| 5,291,560 A | 3/1994 | Daugman |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,348,003 A | 9/1994 | Caro |
| 5,355,880 A | 10/1994 | Thomas et al. |
| 5,360,004 A | 11/1994 | Purdy et al. |
| 5,361,758 A | 11/1994 | Hall et al. |
| 5,372,135 A | 12/1994 | Mendelson et al. |
| 5,379,764 A | 1/1995 | Barnes et al. |
| 5,402,778 A | 4/1995 | Chance |
| 5,419,321 A | 5/1995 | Evans |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,494,032 A | 2/1996 | Robinson et al. |
| 5,515,847 A | 5/1996 | Braig et al. |
| 5,523,054 A | 6/1996 | Switalski et al. |
| 5,533,509 A | 7/1996 | Koashi et al. |
| 5,537,208 A | 7/1996 | Bertram et al. |
| 5,552,997 A | 9/1996 | Massart |
| 5,596,992 A | 1/1997 | Haaland et al. |
| 5,606,164 A | 2/1997 | Price et al. |
| 5,636,633 A | 6/1997 | Messerschmidt et al. |
| 5,655,530 A | 8/1997 | Messerschmidt |
| 5,672,864 A | 9/1997 | Kaplan |
| 5,672,875 A | 9/1997 | Block et al. |
| 5,677,762 A | 10/1997 | Ortyn et al. |
| 5,708,593 A | 1/1998 | Saby et al. |
| 5,719,950 A | 2/1998 | Osten et al. |
| 5,724,268 A | 3/1998 | Sodickson et al. |
| 5,743,262 A | 4/1998 | Lepper, Jr. et al. |
| 5,747,806 A | 5/1998 | Khalil |
| 5,750,994 A | 5/1998 | Schlager |
| 5,782,755 A | 7/1998 | Chance et al. |
| 5,792,050 A | 8/1998 | Alam et al. |
| 5,792,053 A | 8/1998 | Skladnev et al. |
| 5,793,881 A | 8/1998 | Stiver et al. |
| 5,808,739 A | 9/1998 | Turner et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,850,623 A | 12/1998 | Carman, Jr. et al. |
| 5,853,370 A | 12/1998 | Chance et al. |
| 5,860,421 A | 1/1999 | Eppstein et al. |
| 5,886,347 A | 3/1999 | Inoue et al. |
| 5,902,033 A | 5/1999 | Levis et al. |
| 5,914,780 A | 6/1999 | Turner et al. |
| 5,933,792 A | 8/1999 | Andersen et al. |
| 5,935,062 A | 8/1999 | Messerschmidt et al. |
| 5,945,676 A | 8/1999 | Khalil et al. |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |
| 6,005,722 A | 12/1999 | Butterworth et al. |
| 6,016,435 A | 1/2000 | Maruo et al. |
| 6,025,597 A | 2/2000 | Sterling et al. |
| 6,026,314 A | 2/2000 | Amerov et al. |
| 6,031,609 A | 2/2000 | Funk et al. |
| 6,034,370 A | 3/2000 | Messerschmidt |
| 6,040,578 A | 3/2000 | Malin et al. |
| 6,041,247 A | 3/2000 | Weckstrom et al. |
| 6,041,410 A | 3/2000 | Hsu et al. |
| 6,043,492 A | 3/2000 | Lee et al. |
| 6,044,285 A | 3/2000 | Chaiken et al. |
| 6,045,502 A | 4/2000 | Eppstein et al. |
| 6,046,808 A | 4/2000 | Fately |
| 6,049,727 A | 4/2000 | Crothall |
| 6,056,738 A | 5/2000 | Marchitto et al. |
| 6,057,925 A | 5/2000 | Anthon |
| 6,061,581 A | 5/2000 | Alam et al. |
| 6,061,582 A | 5/2000 | Small et al. |
| 6,066,847 A | 5/2000 | Rosenthal |
| 6,070,093 A | 5/2000 | Oosta et al. |
| 6,073,037 A | 6/2000 | Alam et al. |
| 6,078,042 A * | 6/2000 | Fellows .................. 250/252.1 |
| 6,088,605 A | 7/2000 | Griffith et al. |
| 6,100,811 A | 8/2000 | Hsu et al. |
| 6,115,673 A | 9/2000 | Malin et al. |
| 6,141,101 A | 10/2000 | Bleier et al. |
| 6,146,897 A * | 11/2000 | Cohenford et al. .... 250/339.09 |
| 6,147,749 A | 11/2000 | Kubo et al. |
| 6,152,876 A | 11/2000 | Robinson et al. |
| 6,157,041 A | 12/2000 | Thomas et al. |
| 6,175,407 B1 | 1/2001 | Sartor |
| 6,212,424 B1 | 4/2001 | Robinson |
| 6,226,541 B1 | 5/2001 | Eppstein et al. |
| 6,230,034 B1 | 5/2001 | Messerschmidt et al. |
| 6,230,045 B1 * | 5/2001 | Hoogenraad et al. ....... 600/473 |

| | | | |
|---|---|---|---|
| 6,240,306 | B1 | 5/2001 | Rohrscheib et al. |
| 6,241,663 | B1 | 6/2001 | Wu et al. |

FOREIGN PATENT DOCUMENTS

| | | |
|---|---|---|
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |
| EP | 0 801 297 A1 | 10/1997 |
| EP | 0 836 083 A1 | 4/1998 |
| EP | 0 843 986 A2 | 5/1998 |
| EP | 0 869 348 A2 | 10/1998 |
| EP | 0 897 691 A2 | 2/1999 |
| EP | 0 317 121 B1 | 5/1999 |
| EP | 0 982 583 A1 | 3/2000 |
| EP | 0 990 945 A1 | 4/2000 |
| WO | WO 92/00513 | 1/1992 |
| WO | WO 92/17765 | 10/1992 |
| WO | WO 93/00855 | 1/1993 |
| WO | WO 93/07801 | 4/1993 |
| WO | WO 95/22046 | 8/1995 |
| WO | WO 97/23159 | 7/1997 |
| WO | WO 97/27800 | 8/1997 |
| WO | WO 97/28437 | 8/1997 |
| WO | WO 97/28438 | 8/1997 |
| WO | WO 98/01071 | 1/1998 |
| WO | WO 98/37805 | 9/1998 |
| WO | WO 98/40723 | 9/1998 |
| WO | WO 99/09395 | 2/1999 |
| WO | WO 99/37203 | 7/1999 |
| WO | WO 99/43255 | 9/1999 |
| WO | WO 99/46731 | 9/1999 |
| WO | WO 99/55222 | 11/1999 |
| WO | WO 99/56616 | 11/1999 |
| WO | WO 01/15596 | 3/2001 |

OTHER PUBLICATIONS

Anderson, Robert J. et al., "Resolution and Instrument Line Shape Effects on Spectral Compensation with Fourier Transform Infrared Spectrometers," Analytical Chemistry, vol. 50, No. 13, Nov. 1978, pp. 1804–1811.
Anderson, C. E. et al., "Fundamentals of Calibration Transfer Through Procrustes Analysis," Appln. Spectros., vol. 53, No. 10 (1999) p. 1268.
Ashbourn, Julian, Biometrics; Advanced Identity Verification, Springer, 2000, pp. 63–64).
Bantle, John P. et al., "Glucose Measurement in Patients with Diabetes Mellitus with Dermal Interstitial Fluid," Copyright © 1997 by Mosby–Year Book, Inc., 9 pages.
Blank, T.B. et al., "Transfer of Near–Infrared Multivariate Calibrations Without Standards," Anal. Chem., vol. 68 (1996) p. 2987.
Brasunas John C. et al., "Uniform Time–Sampling Fourier Transform Spectroscopy," Applied Optics, vol. 36, No. 10, Apr. 1, 1997, pp. 2206–2210.
Brault, James W., "New Approach to High–Precision Fourier Transform Spectrometer Design," Applied Optics, Vo. 35, No. 16, Jun. 1, 1996, pp. 2891–2896.
Cassarly, W.J. et al., "Distributed Lighting Systems: Uniform Light Delivery," Source Unknown, pp. 1698–1702.
Chang, Chong–Min et al., "An Uniform Rectangular Illuminating Optical System for Liquid Crystal Light Valve Projectors," Euro Display '96 (1996) pp. 257–260.
Coyne, Lawrence J. et al., "Distributive Fiber Optic couplers Using Rectangular Lightguides as Mixing Elements," (Information Gatekeepers, Inc. Brookline, MA, 1979) pp. 160–164.

de Noord, Onno E., "Multivariate Calibration Standardization," Chemometrics and Intelligent Laboratory Systems 25, (1994) pp. 85–97.
Despain, Alvin M. et al., "A Large–Aperture Field–Widened Interferometer–Spectrometer for Arglow Studies," Aspen International Conference on Fourier Spectroscopy, 1970, pp. 293–300.
Faber, Nicolaas, "Multivariate Sensitivity for the Interpretation of the Effect of Spectral Retreatment Methods on Near–Infrared Calibration Model Predictions," Analytical Chemistry, vol. 1, No. 3, Feb. 1, 1999, pp. 557–565.
Geladi, Paul et al., A Multivariate NIR Study of Skin Alterations in Diabetic Patients as Compared to Control Subjects, J. Nera Infrared Spectrosc., vol. 8 (2000) pp. 217–227.
Haaland, David M. et al. "Reagentless Near–Infrared Determination of Glucose in Whole Blood Using Multivariate Calibration," Applied Spectroscopy, vol. 46, No. 10 (1992) pp. 1575–1578.
Harwit, M. et al., "Chapter 5—Instrumental Considerations" Hadamard Transform Optics, Academic Press (1979) pp. 109–145.
Heise H. Michael et al., "Near–Infrared Reflectance Spectroscopy for Noninvasive Monitoring of Metabolites," Clin. Chem. Lab. Med. 2000, 38(2) (2000) pp. 137–145.
Heise, H.M. et al., "Near Infrared Spectrometric Investigation of Pulsatile Blood Flow for Non–Invasive Metabolite Monitoring," CP430, Fourier Transform Spectroscopy: $11^{th}$ International Conference, (1998) pp. 282–285.
Heise, H.M. et al., "Noninvasive Blood Glucose Sensors Based on Near–Infrared Spectroscopy," Artif Organs, vol. 18, No. 6 (1994) pp. 1–9.
Heise, H.M. "Non–Invasive Monitoring of Metabolites Using Near–Infrared Spectroscopy: State of the Art," Horm. Metab. Res., vol. 28 (1996) pp. 527–534.
Hopkins, George W. et al., "In–vivo NIR Diffuse–reflectance Tissue Spectroscopy of Human Subjects," SPIE, vol. 3597, Jan. 1999, pp. 632–641.
Jagemann, Kay–Uwe et al. "Application of Near–Infrared Spectroscopy for Non–Invasive Determination of Blood/ Tissue Glucose Using Neural Networks," Zeitschrift for Physikalische Chemie, Bd.191, S. 179–190 (1995).
Johansen, Ib–Rune et al., "Calibration of an FT–IR Spectrometer for Ambient Air Monitoring Using PLS," Applied Spectroscopy, vol. 51, No. 10 (1997,) pp. 1540–1546.
Khalil, Omar S., "Spectroscopic and Clinical Aspects of Noninvasive Glucose Measurements," Clinical Chemistry, 45:2 (1999) pp. 165–177.
Kohl, Matthias et al., "The Influence of Glucose Concentration Upon the Transport of Light in Tissue–simulating Phantoms," Phys. Med. Biol., vol. 40 (1995) pp. 1267–1287.
Korte, E.H. et al., "Infrared Diffuse Reflectance Accessory for Local Analysis on Bulky Samples," Applied Spectroscopy, vol. 42, No. 1, Jan. 1988, pp. 38–43.
Kumar, G. et al., "Optimal Probe Geometry for Near–Infrared Spectroscopy of Biological Tissue," Applied Spectroscopy, vol. 36 (1997) p. 2286.
Lorber, Avraham et al., "Local Centering in Multivariate Calibration," Journal of Chemometrics, vol. 10 (1996) pp. 215–220.
Lorber, Avraham et al., "Net Analyte Signal Calculation in Multivariate Calibration," Analytical Chemistry, vol. 69, No. 8, Apr. 15, 1997, pp. 1620–1626.
Manasteriski, A. et al. "Blanking and the Determination of Cholesterol," Mikrochimica Acta, (1975 II) pp. 1–16.
Marbach, Ralf, "Measurement Techniques for IR Spectroscopic Blood Glucose Determination," (1994) pp. 1–158.

Marbach, R. et al. "Noninvasive Blood Glucose Assay by Near–Infrared Diffuse Reflectance Spectroscopy of the Human Inner Lip," Applied Spectroscopy, vol. 47, No. 7 (1993) pp. 875–881.
Marbach, R. et al. "Optical Diffuse Reflectance Accessory for Measurements of Skin Tissue by Near–Infrared Spectroscopy," Applied Optics, vol. 34, No. 4, Feb. 1, 1995, pp. 610–621.
Mardia, K.V. et al., Multivariate Analysis, Academic Press (1979) pp. 300–325.
Martens, Harald et al., Updating Multivariate Calibrations of Proceed NIR Instruments, Adv. Instru. Control (1990) pp. 371–381.
McIntosh, Bruce C. et al. Quantitative Reflectance Spectroscopy in the Mid–IR, $16^{th}$ Annual FACSS Conference, Oct. 1989.
Nichols, et al., Design and Testing of a White–Light, Steady–State Diffuse Reflectance Spectrometer for Determination of Optical Properties of Highly Scattering Systems, Applied Optics, Jan. 1, 1997, 36(1), pp 93–104.
Offner, A., "New Concepts in Projection Mask Aligners," Optical Engineering, vol. 14, No. 2, Mar.–Apr. 1975, pp. 130–132.
Osborne, B.G. et al., "Optical Matching of Near Infrared Reflectance Monochromator Instruments for the Analysis of Ground and Whole Wheat," J. Near Infrared Spectrosc., vol. 7 (1999) p. 167.
Ozdemir, D. et al., "Hybrid Calibration Models: An Alternative to Calibration Transfer," Appl. Spectros., vol. 52, No. 4 (1998) p. 599.
Powell, J.R. et al, "An Algorithm for the Reproducible Spectral Subtraction of Water from the FT–CR Spectra of Proteins in Dilute Solutions and Adsorbed Monolayers," Applied Spectroscopy, vol. 40, No. 3 (1986) pp. 339–344.
Ripley, B.D. Pattern Recognition and Neural Networks, Cambridge University Press (1996) pp. 91–120.
Robinson, M. Ries et al., "Noninvasive Glucose Monitoring in Diabetic Patients: A Preliminary Evaluation," Clinical Chemistry, vol. 38, No. 9 (1992) pp. 1618–1622.
Royston, David D. et al., "Optical Properties of Scattering and Absorbing Materials Used in the Development of Optical Phantoms at 1064 NM," Journal of Biomedical Optics, vol. 1, No. 1, Jan. 1996, pp. 110–116.
Rutan, Sarah C. et al., "Correction for Drift in Multivariate Systems Using the Kalman Filter," Chemometrics and Intelligent Laboratory Systems 35, (1996) pp. 199–211.
Salit, M.L. et al., "Heuristic and Statistical Algorithms for Automated Emission Spectral Background Intensity Estimation," Applied Spectroscopy, vol. 48, No. 8 (1994) pp. 915–925.
Saptari, Vidi Alfandi, "Analysis, Design and Use of a Fourier–Transform Spectrometer for Near Infrared Glucose Absorption Measurement," (Massachusetts Institute of Technology, 1999) pp. 1–76.
Schmitt, J.M. et al., "Spectral Distortions in Near–Infrared Spectroscopy of Turbid Materials," Applied Spectroscopy, No. 50 (1996) p. 1066.
Service, F. John et al., Dermal Interstitial Glucose as an Indicator of Ambient Glycemia, Diabetes Care, vol. 20, No. 9, Sep. 1997, 9 pages.
Shroder, Robert, (Internet Article) MicroPac Forum Presentation, Current performance results, May 11, 2000.

Sjoblom, J. et al., "An Evaluation of Orthogonal Signal correction Applied to Calibration Transfer of Near Infrared Spectra," Chemom & Intell Lab. Sys., vol. 44 (1998) p. 229.
Spitz, Henry et al., "A New Anthropometric Phantom for Calibrating In Vivo Measurements of Stable Lead in the Human Leg Using X–ray Fluorescence," Health Physics, vol. 78, No. 2, Feb. 2000, pp. 159–169.
Steel, W.H., "Interferometers for Fourier Spectroscopy," Aspen International Conference on Fourier Spectroscopy, (1970) pp. 43–53.
Sternberg R.S. et al., "A New Type of Michelson Interference Spectrometer," Sci. Instrum., vol. 41 (1964) pp. 225–226.
Stork, Chris L. et al., "Weighting Schemes for Updating Regression Models—a Theoretical Approach," Chemometrics and Intelligent Laboratory Systems 48, (1999) pp. 151–166.
Sum, Stephen T. et al., "Standardization of Fiber–Optic Probes for Near–Infrared Multivariate Calibrations," Applied Spectroscopy, vol. 52, No. 6 (1998) pp. 869–877.
Swierenga, H. et al., "Comparison of Two Different Approaches Toward Model Transferability in NIR Spectroscopy," Applied Spectroscopy, vol. 52, No. 1 (1998) pp. 7–16.
Swierenga, H. et al., "Improvement of PLS Model Transferability by Robust Wavelength Selection," Chemometrics and Intelligent Laboratory Systems, vol. 41 (1998) pp. 237–248.
Swierenga, H. et al., "Strategy for Constructing Robust Multivariate Calibration Models," Chemometrics and Intelligent Laboratory Systems, vol. 49, (1999) pp. 1–17.
Teijido, J.M. et al., "Design of a Non–conventional Illumination System Using a Scattering Light Pipe," SPIE, Vo. 2774 (1996) pp. 747–756.
Teijido, J.M. et al., "Illumination Light Pipe Using Micro–Optics as Diffuser," SPIE, vol. 2951 (1996) pp. 146–155.
Thomas, Edward V. et al., "Development of Robust Multivariate Operation Models," Technometrics, vol. 42, No. 2, May 2000, pp. 168–177.
Tipler, Paul A., Physics, Second Edition, Worth Publishers, Inc., Chapter 34, Section 34–2, Nov. 1983, pp. 901–908.
Wang, Y–D. et al., "Calibration Transfer and Measurement Stability of Near–Infrared Spectrometers," Appl. Spectros., vol. 46, No. 5 (1992) pp. 764–771.
Wang, Y–D. et al., "Improvement of Multivariate Calibration Through Instrument Standardization," Anal. Chem., vol. 64 (1992) pp. 562–564.
Waag, Z., "Additive Background Correction in Multivariate Instrument Standardization," Anal. Chem., vol. 67 (1995) pp. 2379–2385.
Ward, Kenneth J. et al., "Post–Prandial Blood Glucose Determination by Quantitative Mid–Infrared Spectroscopy," Applied Spectroscopy, vol. 46, No. 6 (1992) pp. 959–965.
Webb, Paul, "Temperatures of Skin, Subcutaneous Tissue, Muscle and Core in Resting Men in C—, Comfortable and Hot Conditions," European Journal of Applied Physiology, vol. 64 (1992) pp. 471–476.
Whitehead, L.A. et al., "High–efficiency Prism Light Guides with Confocal Parabolic Cross Sections," Applied Optics, vol. 37, No. 22 (1998) pp. 5227–5233.

* cited by examiner

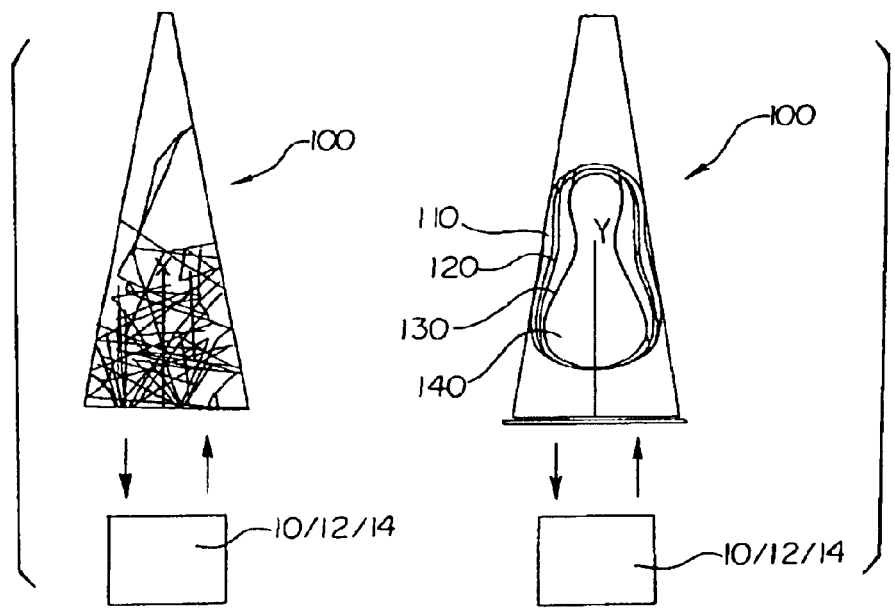
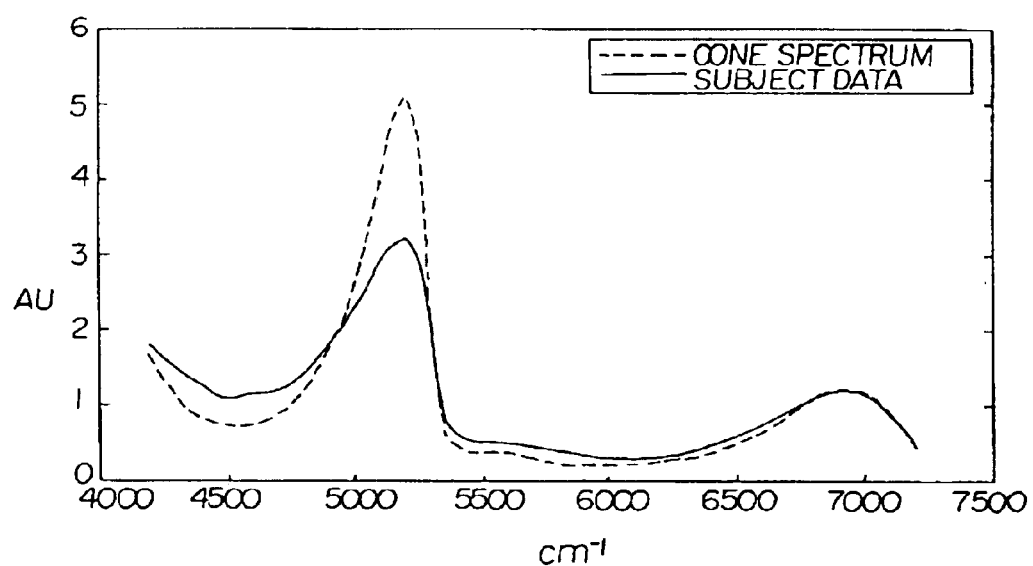

OPTICALLY SIMILAR REFERENCE SAMPLES AND RELATED METHODS FOR MULTIVARIATE CALIBRATION MODELS USED IN OPTICAL SPECTROSCOPY

RELATED APPLICATIONS

This application is related to U.S. patent application Ser. No. 09/832,585 now U.S. Pat. No. 6,574,490, entitled "System for Non-Invasive Measurement of Glucose in Humans"; U.S. patent application Ser. No. 09/832,586 now U.S. Pat. No. 6,862,091, entitled "Illumination Device and Method for Spectroscopic Analysis"; and U.S. patent application Ser. No. 09/832,631, entitled "Encoded Variable Filter Spectrometer", all filed on the same date herewith and assigned to the assignee of the present application. The disclosure of each of these related applications is hereby incorporated by reference.

FIELD OF THE INVENTION

The present invention generally relates to calibration reference samples and techniques for multivariate calibration models used in optical spectroscopy. More specifically, the present invention relates to calibration reference samples and techniques for building and maintaining multivariate calibration models used in optical spectroscopy for the measurement of analytes in bodily tissue by utilizing a reference sample that is optically similar to the analyte containing tissue.

BACKGROUND OF THE INVENTION

The need for an accurate and non-invasive method for determining attributes of or analyte concentrations in bodily tissues, bodily fluids or other biological samples is well documented. For example, accurate non-invasive measurement of blood glucose levels in diabetic patients would greatly improve diabetes treatment. U.S. Pat. No. 5,379,764 to Barnes et al. discloses the necessity for diabetics to frequently monitor blood glucose levels. The more frequent the blood glucose levels are measured, the less likely the occurrence of large swings in blood glucose levels. These large swings are associated with the very undesirable short-term symptoms and long-term complications of diabetes. Such long-term complications include heart disease, arteriosclerosis, blindness, stroke, hypertension, kidney failure, and premature death.

Several systems have been proposed for the non-invasive measurement of blood glucose levels. However, despite these efforts, direct and invasive measurements (e.g., blood sampling by a lancet cut into the finger) are still necessary for most if not all presently FDA approved and commercially available glucose monitors. This is believed so compromising to the diabetic patient that frequent blood glucose measurement, which is necessary to ensure effective diabetes management, is rarely achieved.

The various proposed non-invasive methods for determining blood glucose level generally utilize quantitative infrared spectroscopy as a theoretical basis for analysis. In general, these methods involve probing glucose containing tissue using infrared radiation in transmission or in diffuse reflectance. It is known that glucose absorbs at multiple frequencies in both the mid- and near-infrared range. There are, however, other infrared active analytes in the tissue and blood that also absorb at similar frequencies. Due to the overlapping nature of these absorption bands, no single or specific frequency can be used for reliable non-invasive glucose measurement. Analysis of spectral data for glucose measurement thus requires evaluation of many spectral intensities over a wide spectral range to achieve the sensitivity, precision, accuracy, and reliability necessary for quantitative determination.

U.S. Pat. No. 4,975,581 to Robinson et al. discloses a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also may be any chemical or physical property of the sample. The method of Robinson et al. involves a two-step process that includes both calibration and prediction steps.

In the calibration step, the infrared light is coupled to calibration samples of known characteristic values so that there is differential attenuation of at least several wavelengths of the infrared radiation as a function of the various components and analytes comprising the sample with known characteristic value. The infrared light is coupled to the sample by passing the light through the sample or by reflecting the light from the sample. Absorption of the infrared light by the sample causes intensity variations of the light that are a function of the wavelength of the light. The resulting intensity variations are measured for the set of calibration samples of known characteristic values. Original or transformed intensity variations are then empirically related to the known characteristic of the calibration samples using a multivariate algorithm to obtain a multivariate calibration model. The model preferably accounts for subject variability (both intra-subject and inter-subject), instrument variability and environment variability.

A further method of building a calibration model and using such model for prediction of analytes in or attributes of tissue is disclosed in commonly assigned U.S. Pat. No. 6,157,041 to Thomas et al., entitled "Method and Apparatus for Tailoring Spectrographic Calibration Models," the disclosure of which is incorporated herein by reference.

In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic of the unknown sample.

As mentioned above, the multivariate calibration model preferably accounts for instrument variability and environment variability. In addition, it is desirable that the model accounts for such variability over time. In other words, in the practical use of a multivariate calibration model, it is desirable that prediction errors or model applicability remain stable over time. It is known that prediction errors can be caused by changes in the measuring instrument or the measurement environment over time. See, for example, H. Swierenga, et. al., *Applied Spectroscopy*, Vol. 52, No. 1, 1998. As instruments change or drift over time, they produce variations in the spectra that reduce the ability of a calibration model to make accurate predictions. In order to maintain a multivariate calibration over time, the effect/magnitude of these variations must be reduced as much as possible.

One approach involves manipulating the calibration model itself. The most basic method is re-calibrating the instrument. In other words, when the multivariate model becomes invalid, due to a drift in the instrument response, the entire calibration procedure is repeated. This is a time and labor-intensive process, and, if the original calibration samples are unstable, a completely new set of samples must be prepared, which is not always practical. Because of the amount of effort involved in re-calibrations, this option is not a favorable one. Furthermore, for non-invasive in-vivo calibration models, there may be a complete lack of viable samples for re-calibration.

Another approach is to update the calibration model when the prediction samples begin to drift out of the calibration model space. This is especially useful in process monitoring, and can be achieved through the addition of new calibration samples that reflect changing analytical conditions. See, for example, Stork, Chris L.; Kowalski, Bruce R., *Chemom. Intell. Lab. Syst.* (1999), 48(2), 151–166; and Martens, H.; Westad, F.; Foulk, S.; Bernsten, H., *Adv. Instrum. Control* (1990), 45(Pt. 1), 371–381. This is less labor-intensive than an entire re-calibration since it only involves adding data from the new instrument state to the original calibration model data set. The problem with this approach is that it requires on-going data monitoring with a reliable method to evaluate when an update to the model is necessary. The method must also distinguish between an instrumental change that is normal and an instrumental change that indicates a problem that must be fixed (such as a component failure) so that the model is not simply updated with "bad" data. Thus, it can be difficult to ascertain at what point an update to the model becomes necessary while also establishing that the instrument itself is not failing.

Another approach for maintaining calibration is to build the calibration data set in such a way that expected instrumental variations are incorporated into the data. In other words, the calibration design should cover all relevant sources of variation that might be seen in future samples, so that future samples will not appear "unusual". See, for example, Swierenga, H.; de Weijer, A. P.; van Wijk, R. J.; Buydnes, L. M. C., *Chemom. Intell. Lab. Syst.* (1999), 49(1), 1–17; De Noord, O. E., *Chemom. Intell. Lab. Syst.* (1994), 25, 85–97; and Thomas, E. V.; Ge, N., *Technometics*, (2000), 42(2), 168–176. Calibration samples must therefore be measured at different instrumental states and at different environmental conditions. A disadvantage of this approach is that it requires the burdensome task of measuring many more calibration samples to provide enough degrees of freedom to estimate the additional parameters. Another disadvantage is that it is often difficult to foresee all relevant variation sources. This creates the possibility that the instrument state may vary outside the model space despite the experimental design. When a variation occurs that is not accounted for in the model, the calibration will no longer be valid.

A related approach is to utilize an instrument-standardization technique for mapping the instrument in one state to an instrument in another state. See, De Noord, O. E., *Chemom. Intell. Lab. Syst.* (1994), 25, 85–97. This technique works best with a selection of "real" samples, which means that the transfer samples should ideally be a subset of those from the calibration set. However, it is often difficult to span the relevant data space with "generic" samples, and "real" calibration samples are often not reproducible and, therefore, impractical.

Yet another approach is to use mathematical pre-processing techniques to correct for the spectral variations caused by instrument drift over time. For example, such pre-processing methods include the use of first and second derivatives and other mathematical techniques to correct for constant and sloping baselines, and the use of Kalman filters to correct for drift. See, for example, Faber, N. M., *Anal. Chem.* (1999), 71(3), 557–565; Johansen, I. B.; Lines, G. T.; Honne, A.; Midtgaard, T., *Appl. Spectrosc.,* (1997), 51(10), 1540–1546; and Rutan S C, Bouveresse E, Andrew K N, Worsfold P J, Massart D L, *Chemometrics And Intelligent Laboratory Systems*, (1996) 35(2) 199–211. Pre-processing methods inherently rely on assumptions about the instrument's spectral response. If the assumptions do not hold true, then the spectra will not be corrected sufficiently for the model to provide an accurate prediction. The further away the assumption is from reality, the more residual variation will remain in the spectrum and the more artifacts will be added to the spectrum. Such residual variations and artifacts seriously compromise the measurement of small concentrations of analyte, because even a small uncertainty in a large background signal creates a much larger uncertainty in the small analyte signal. Powell, J. R.; Wasacz, F. M.; Jakobsen, R. J., *Appl. Spectrosc.*, (1986), 40(3), 339–344.

A variation of this approach is to calculate a background spectrum based on some assumptions, and then subtract that background spectrum from the sample spectrum. Because a static measure of the background will not compensate for background shifts due to instrument changes, different algorithms (statistical tests and heuristic spectral interpretation) may be used to estimate the background signal for subtraction from the sample response. See, for example, Salit, M. L.; Collins, J. B.; Yates, D. A., *Appl. Spectrosc.,* (1994), 48(8), 915–925. However, as with the other pre-processing techniques described previously, this method also relies on assumptions that may not hold true and may introduce artifacts. Thus, as with all methods that involve estimators, this method is not sufficiently sensitive to estimate the background when the analyte signal is much smaller than the background signal.

As in some of the scientific literature discussed above, several of the patents discussed below disclose methods of dealing with changes in the baseline response of the instrument, where the goal is to isolate individual absorption peaks from the rest of the baseline instrument response. These techniques are applied to univariate spectral measurements, frequently in either plasma or fluorescence spectroscopy. However, none of these patents addresses the use of background measurements for the maintenance of a calibration model as in the present invention.

Franklin (U.S. Pat. No. 4,346,998) discusses measuring individual emission lines using plasma spectroscopy. Franklin describes a spectral background corrector system which causes wavelength scanning or modulation that allows specific absorption peaks to be identified and isolated. Again, Franklin does not offer a method for maintenance of multivariate calibration models over time as in the present invention.

U.S. Pat. No. 5,850,623 to Carman, Jr. et al. and European Patent Application No. 982 583 to Spragg discuss using standard "blank" samples to help reduce the effects of instrument changes. Carman discloses a method for standardizing Raman spectrometers using a reference sample for standardizing the optical instrument. Carman teaches that the choice of the reference sample is arbitrary, and Carman makes no mention of attempting to match the optical characteristics of the reference sample to the sample of interest. Carman suffers from the same limitations as the industry standard use of "blank" samples. Specifically, "blank" samples are spectrally dissimilar from the sample of interest being measured. In addition, "blank" samples or any other dissimilar background are not sufficiently sensitive to estimate the background when the analyte signal is much smaller than the background signal.

Spragg deals directly with attempting to measure the state of a scanning FTIR instrument for spectral correction. Spragg discloses a method of using PCA decomposition to reduce the amount of time required to obtain a useable background reference measurement. The background sample is described as being an empty sample holder. Spragg does not address the limitations of dissimilar backgrounds.

U.S. Pat. No. 5,830,133 to Osten et al. and U.S. Pat. No. 5,360,004 to Purdy et al. discuss mathematical data processing methods to deal with different types of measurement variance. Osten et al. deal with the effects of varying water pathlengths in the sample of interest by using a two compartment mathematical model to describe the sample. Purdy et al. describe the use of data preprocessing steps to reduce the effects of instrument variation by using derivatives of the spectral data. Neither Osten et al. nor Purdy et al. use a reference measurement, and both are inadequate for correcting for the types of instrument variation addressed by the present invention.

In summary, there is no generally accepted means of maintaining multivariate calibrations since none of the methods and theirs associated reference sample is a general solution to the problem. Moreover, when maintaining calibrations for samples where the analyte spectral absorption is much smaller than the gross sample spectrum, there is no known standard procedure to follow. In most other situations, it may be sufficient to use one of the techniques mentioned above, but when the analyte signal is very small, no known method is believed adequate, and spectral changes cannot simply be removed by an offset and/or slope correction. Subtle changes in the spectra must be accounted for in order to successfully maintain the calibration. None of the traditional methods does this, and predictive ability is, therefore, diminished with time.

To the extent that the methods described above use background samples, they do not use optically similar background samples to help maintain multivariate calibrations. An optically similar reference sample is a sample that optically interacts with the optical measurement system in a manner that simulates to a desired degree the optical interaction between the optical system and the test sample. One component of optical similarity is the creation of a spectral absorbance at selected wavelengths that is similar to the test sample. The result is similarly shaped spectra at these wavelengths for both the reference and measurement samples. To obtain a similar shape and matched average absorbance, the optically similar reference sample should absorb the same or similar intensity of light at each selected wavelength over the range of wavelengths measured. An optically dissimilar reference sample is a sample that optically interacts with the optical measurement system in a manner that does not adequately represent the instrument or environmental state. When a dissimilar reference is used, it generally consists of either air or the solvent in which the analyte of interest is dissolved (e.g., an empty sample holder). In cases where the spectral signature of the analyte of interest is large compared to the spectral features due to any other component in the system, the use of an empty sample holder may be sufficient to maintain a stable calibration model over time. Calibration in this instance is typically implemented by forming the ratio of the transmission spectrum of the unknown sample to the transmission spectrum of the reference sample. However, in cases where the spectral signature of the analyte of interest is much smaller than that of the other system components (e.g., glucose levels in blood or other aqueous solution), an empty sample holder or any other sample that is optically different from the prediction sample is not sufficient as a reference sample and is not effective for maintaining calibration.

There is a substantial need for devices and methods that maintain a stable multivariate calibration model designed for quantitative optical spectroscopic measurement of attributes or analytes in bodily tissue, blood or other biological samples. Such devices and methods are especially needed when the spectral absorbance of the attribute or analyte is small relative to the background.

SUMMARY OF THE INVENTION

The present invention provides systems and methods for establishing and/or maintaining the prediction capability over time of a multivariate calibration model designed for quantitative optical spectroscopic measurement of attributes of or analytes in bodily tissues, bodily fluids or other biological samples, including plant samples, animal samples, food products, and derivatives thereof (e.g., human tissue, cheese, fruit, etc.). The present invention is particularly useful in spectroscopic measurement of attributes or analytes when the spectral absorbance of the attribute or analyte is small relative to the background, and stable calibration samples are not readily available. To accomplish this, the present invention uses an optically similar reference sample. An optically similar reference sample is used to capture variation present in the optical system in a manner that enables prediction performance to be maintained. The ability to capture instrument and environmental variation is enhanced by the use of an optically similar reference sample. The optically similar reference sample will be similar to the test sample in terms of spectral radiance. The similar background is preferably reproducible over time and is designed such that its optical properties are sufficiently matched to the sample of interest that instrument and environmental variations are captured in a similar manner in both the sample of interest and the optically similar reference sample.

The present invention is preferably used to analyze biological tissue. Further complexity may be present when biological tissue is the sample of interest. Biological tissue is commonly characterized as a turbid medium. Turbid media generally fail to permit any single ray of light from following an undisturbed pathway through the medium. In effect, turbid media are non-deterministic. That is, a light ray that enters a turbid medium may undergo several scattering events before finally exiting the medium. When many light rays are directed into a turbid medium, each of the exiting rays collected at any given point will have traveled a different distance through the medium. As a result, a spectrum from a turbid medium source is determined not only by type and concentration of the molecular species in the medium, but also by the shape of the pathway distribution the light took to travel through the medium. In the case of human tissue, the primary constituent is water. With respect to tissue, a reasonable water concentration is 75% by volume. Due to the fact that light entering the tissue undergoes multiple scattering interactions, the light rays exiting the tissue will have traveled different pathlengths through the tissue and through the primary constituent water. The resulting spectrum is the summation of many different light rays that have traveled different pathlengths through water. Thus, a spectrum of tissue is composed of many different pathlengths of water. It has been found that an optically similar reference sample of the present invention that optically interacts with the optical measurement system in a manner that simulates tissue preferably produces an optical interaction that results in multiple different pathlengths of water.

As used herein, the calibration model is any set of coefficients or associated algorithms that are used in the generation of a prediction result. The test sample is the sample in which the measurement of the attribute is being made. The reference spectrum is any optical measurement information obtained in conjunction with the optically similar reference sample, and can be full spectrum in nature or any part of the measured response, to include individual wavelengths, and covers information derived from the reference spectrum.

The similar background of the present invention may be quantitatively described in terms of spectral radiance ($W/m^2Sr$=watts per square meter per steradian). Preferably, the similar background preserves substantially the same mapping of input spectral radiance ($W/m^2Sr$) to spectral radiant excitance ($W/m^2Sr$) of the sample of interest. This definition of spectral similarity can be broken down into several sub-categories, all of which are implicitly incorporated into spectral radiance: spectral absorption features, overall light intensity received by the optical detector elements, angular distribution of light emitted by the sample, and spatial distribution of light emitted by the sample. The degree of spectral similarity required for calibration maintenance is dependent on the types and magnitudes of instrumental and environmental variations for which the model must compensate as well as the sensitivity of the model to those variations and the level of the signal due to the analyte. Preferably, the similar background of the present invention provides spectral, spatial and angular similarity as defined hereinafter.

As stated above, the similar background of the present invention is useful for establishing and maintaining a quantitative calibration model for measuring an analyte or attribute whose spectral signature is much smaller than that of the surrounding matrix in a sample of interest. The sample of interest refers to the analyte-containing or attribute-containing spectral sample, such as human bodily tissue (e.g. skin), human bodily fluid (e.g., blood) or other biological sample, whose composition or physical properties are being determined or measured. The use of an optically similar reference sample for calibration maintenance is applicable to several different methods of optical spectroscopy, including reflectance and transmission spectroscopy, for both in vivo and in vitro measurements.

The present invention is particularly suitable for, but not limited to, the following applications. The present invention may be used in combination with a spectrometer for the measurement of blood constituents including glucose, alcohol, BUN (blood urea nitrogen), bilirubin, hemoglobin, creatin, cholesterol, and electrolytes as disclosed in U.S. Pat. No. 5,830,132 to Robinson, entitled Robust Accurate Non-Invasive Analyte Monitor, the entire disclosure of which is hereby incorporated by reference. The present invention may also be used to spectroscopically monitor kidney dialysis as disclosed in U.S. patent application Ser. No. 09/182,340, filed Oct. 29, 1998, entitled "Apparatus and Method for Determination of the Adequacy of Dialysis by Non-Invasive Near-Infrared Spectroscopy", the entire disclosure of which is hereby incorporated by reference. The present invention may also be used to spectroscopically identify people as disclosed in U.S. patent application Ser. No. 09/415,594, filed Oct. 8, 1999, entitled "Apparatus and Method for Identification of Individuals by Near-Infrared Spectrum", the entire disclosure of which is hereby incorporated by reference. The present invention may further be used to maintain classification calibration models such as those used for distinguishing between malignant and benign tumors. Those skilled in the art will recognize that the present invention has other applications not specifically mentioned herein.

The optically similar reference sample may include one or more components or constituents which are optically measured in a manner which closely mimics the optical measurement of the test sample of interest. The construction and composition of the optically similar reference sample depends on a number of factors, including: the wavelength region of light used, the optical properties of the sample of interest, and the type of spectroscopic instrumentation being used. In order to achieve spectral similarity, the optically similar reference sample may contain some of the same components or constituents as the sample of interest (e.g., water, collagen, protein, lipids). The components used to create optical similarity can be natural animal or plant products or can also be synthesized. Specifically organic polymers could be used in the creation of the reference sample. It may also include a concentration of the analyte of interest being measured. Spectral similarity may also be achieved by using alternative components (e.g., optical filter coatings, optical scattering media, or diffuse reflectance material) with spectral characteristics similar to the components and constituents contained in the sample of interest.

The present invention provides a number of different embodiments for the optically similar reference sample. In each of these embodiments, the optically similar reference sample creates a spectral absorbance that is similar to the test sample. In other words, the optically similar reference sample absorbs the same or similar intensity of light at each wavelength over the range of wavelengths measured. Additionally, the optically similar reference sample can absorb a similar relative intensity of light at each selected wavelength over the range of wavelengths measured. The similar relative absorbance will result in a similar spectral shape, while the average absorbance value of the resulting spectra may be different. With this in mind, those skilled in the art will recognize that there are other types of reference samples that may be employed without departing from the scope or spirit of the present invention. Thus, the following examples are provided for purposes of illustration, not limitation.

The optically similar reference sample may include an optically transparent layer or container, a diffusing layer, and a constituent layer disposed therebetween. The constituent layer may contain the same or similar constituents contained in the test sample of interest, such as water, collagen or lipid. The diffusing layer may be cone shaped or relatively flat with an irregular (non-planar) surface.

The optically similar reference sample may alternatively include a container that is at least partially optically transparent and a scattering solution disposed therein. The optically similar reference sample may also include a stirring mechanism for stirring the scattering solution. The scattering solution may comprise reflective beads disposed in a constituent such as water or a collagen gel.

As another alternative, the optically similar reference sample may comprise multiple layers including a first optical splitting layer, a reflective layer; a first constituent layer disposed between the first optical splitting layer and the reflective layer, a second optical splitting layer, and a second constituent layer disposed between the first optical splitting layer and the optical splitting transparent layer. The multilayer reference sample may include more altering optical splitting layers and constituent layers. Again, the constituent layer may comprise water, collagen or lipid.

As a further alternative, the optically similar reference sample may include a container that is at least partially optically transparent, a constituent disposed in the container, and a spacer disposed in the container. This arrangement may be referred to as a transmission cell. Preferably, multiple spacers are disposed in the container and the spacers displace water or other liquid to create a background with several different length water or other liquid paths.

As yet another alternative, the optically similar reference sample may include an optically transparent layer, and a diffuse reflective layer (e.g., Spectralon), and a constituent layer disposed between the optically transparent layer and the diffuse reflective layer. The diffuse reflective layer is movable relative to the optically transparent layer to change the distance or height therebetween.

The optically similar reference sample may alternatively include a container that is at least partially optically transparent and an animal (e.g., bovine, porcine) based bodily constituent disposed therein. The animal based bodily constituent may comprise an animal bodily tissue (e.g., skin), an animal bodily fluid (e.g., blood).

The method of the present invention also provides a system in which any of these optically similar reference sample may be used. The optical spectroscopy system may include an optical spectrometer having an illumination source (e.g., NIR), a collection system, and a reference sample optically coupled (e.g., disposed adjacent) to the illumination source and collection system. The background sample may be measured using the exact same system and methodology as that used for the test sample of interest. Alternatively, the background sample may have a separate interface with the instrument. In some embodiments, the optically similar reference sample is composed of multiple components that are simultaneously measured at different locations in the optical path of the spectroscopic instrument. In most embodiments, the optically similar reference sample may be designed for either manual or automatic placement into the correct location for optical sampling. In the case of automatic placement, this design allows for automated obtainment of the reference spectrum and would enable calibration maintenance without the direct intervention of an operator.

The present invention also provides a method of establishing an accurate calibration model and/or maintaining the accuracy of the optical measurement system by using an optically similar reference sample as described above. In one preferred embodiment, a reference spectrum is obtained from the optically similar reference sample using an optical system and the calibration model is created or modified based on use of the calibration data and the reference spectrum. One such method is to use a linear combination of the calibration data and reference spectra. The combinations of calibration data and reference data can be done in a structured or random way. It been found that random associations work effectively and are easily implemented. The process of creating these composite data is referred to as robustification. The resulting calibration spectra contain the reference spectra from the optically similar reference spectrum combined with calibration data. The resulting data contains spectroscopic variation associated with the instrument and environmental state of the instrument. The composite calibration data can be processed to develop a calibration model. Utilizing the newly created or modified calibration model, an analyte or attribute of the test sample is predicted based on the test spectrum. In another preferred embodiment, the prediction of the analyte or attribute of the test sample may be based on a test spectrum that has been modified by the reference spectrum. The modified test spectrum is used as an input to create the model or as input to an existing model to predict the analyte or attribute. The modification by, or use of, the reference spectrum helps compensate for, or account for, instrument or environmental changes. In another embodiment, multiple optically similar reference samples are used to create multiple reference spectra.

Preferably, the reference spectrum is obtained just prior to obtaining the test spectrum. To increase accuracy, multiple reference spectra may be obtained near in time to obtaining the test spectrum. The multiple reference spectra may be obtained over a period of time and time-averaged or exponentially time-weighted just prior to obtaining the test spectrum.

The present invention provides a number of advantages over the prior art. As stated previously, the present invention utilizes an optically similar reference sample to allow a multivariate calibration model to be maintained over long periods of time such that it does not become invalid for future spectral predictions. The optically similar reference sample of the present invention is useful in situations where the analyte of interest has a signal that is much smaller than the absorbing background of the sample matrix, since prior art methods do not successfully maintain calibration in the same situation. As compared to the prior art method of updating calibration, the present invention does not require periodic updating nor does it interfere with evaluation of instrument condition. As compared to the prior art method of incorporating all predictable variations into the calibration model, the present invention does not rely on any predictions, which may prove to be untrue and thereby invalidate the calibration. As compared to the prior art method of instrument-standardization using generic and real samples, the similar background of the present invention allows the instrument state to be appropriately represented, while eliminating the need for real samples which are often unstable or not reproducible over time. As compared to the mathematical pre-processing techniques of the prior art, the present invention allows the instrument response to be seen in the same way as the sample of interest and therefore does not rely on possibly false or inaccurate assumptions regarding instrument response. The present invention thus provides an improvement over these prior art methods because spectroscopic variation due to instrument or environmental changes are effectively captured through the use of an optically similar reference sample. The use of an optically similar reference sample enables a variety of methods to effectively compensate for unmodeled variations or artifacts, thereby allowing accurate predictions to be made.

BRIEF DESCRIPTION OF THE DRAWINGS

FIGS. 5 and 6 illustrate a cone background device in accordance with an embodiment of the present invention, wherein FIG. 5 illustrates a ray-trace of the cone background device and FIG. 6 illustrates a partial cut-away view of the cone background device;

FIG. 7 shows a graph of spectral response demonstrating the spectral match between the tissue sample and the cone background;

DETAILED DESCRIPTION OF THE INVENTION

Figure 1:
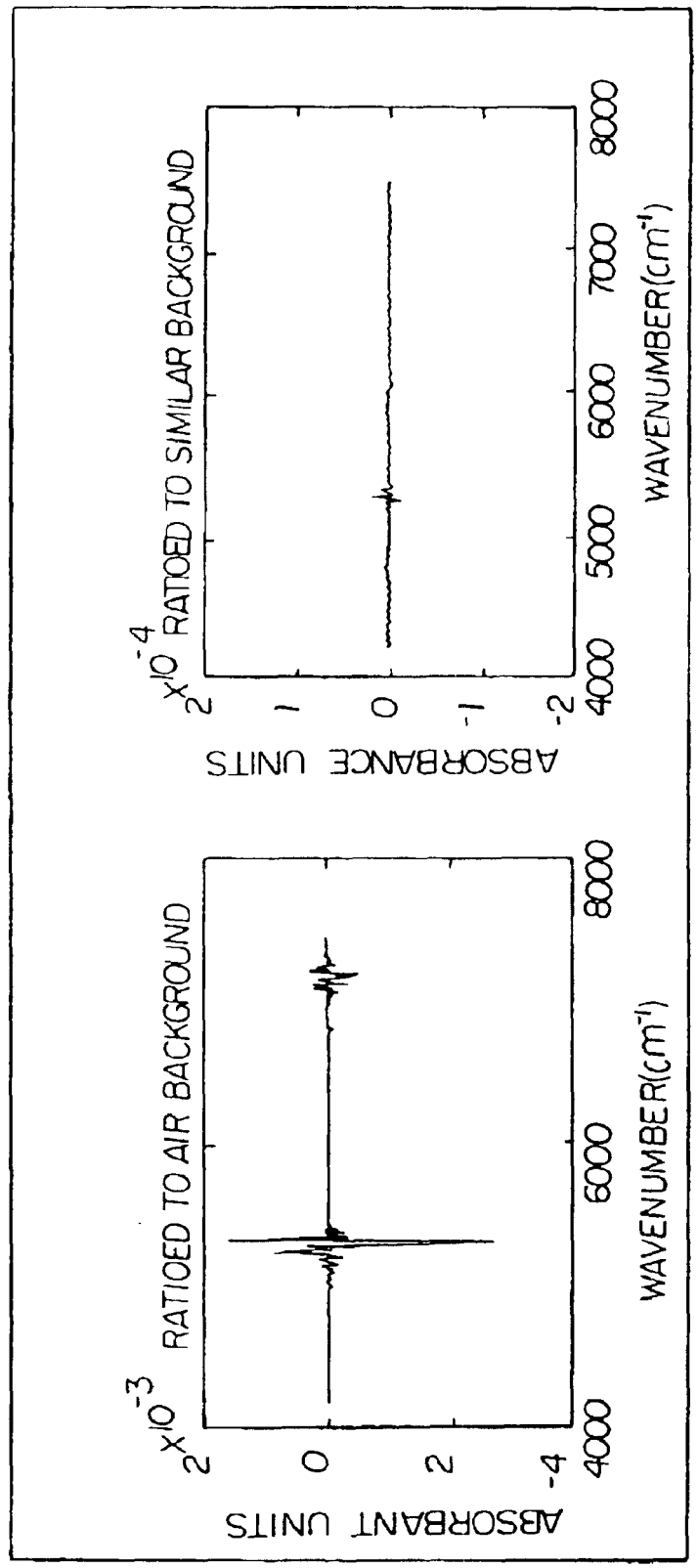
FIG. 1 shows two graphs of spectral residuals comparing a conventional air background to a similar background in accordance with the present invention.

The following detailed description should be read with reference to the drawings in which similar elements in different drawings are numbered the same. The drawings, which are not necessarily to scale, depict illustrative embodiments and are not intended to limit the scope of the invention.

To better appreciate the benefits afforded by the present invention, it is useful to analytically review the problem at hand. The problem solved by the present invention is the difficulty in maintaining a multi-wavelength calibration model for quantitatively measuring the concentration of analytes whose spectral absorption is much smaller than that of the gross sample spectrum. The cause of the failure of a spectrally dissimilar reference sample to maintain calibration under these conditions can be described analytically as shown below.

It has been shown in the literature that photometric inaccuracies will be present even in an ideal instrument of finite resolution where all sources of non-linearity (detector response, stray light, etc.) have been removed. See, for example, R. J. Anderson and P. R. Griffiths, *Analytical Chemistry*, Vol. 47, No. 14, December 1975; and R. J. Anderson and P. R. Griffiths, *Analytical Chemistry*, Vol. 50, No. 13, November 1978. This inherent inaccuracy is caused by the finite resolution of the instrument (grating spectrometer or FT interferometer) because a spectrum produced by an instrument with finite resolution will be the true sample spectrum convolved with the instrument line shape (ILS) (for a grating spectrometer, the ILS is a function of the entrance and exit slit widths and for an FT interferometer, the ILS is a function of the instrument self-apodization and the apodization function used in performing the Fourier transform). One can think of the convolution process as a distortion of the true spectrum at a particular wavenumber that is dependent on all other spectral intensities within the spectral bandpass of the instrument. Mathematically this can be written as Equation (1):

$$T^a(\bar{v}_i) = \int_0^\infty \sigma(\bar{v} - \bar{v}_i) e^{-K(\bar{v})l} d\bar{v} \qquad \text{Eq. (1)}$$

where $T^a(\bar{v}_i)$ is the measured (or apparent) transmission at a particular optical frequency, $\bar{v}_i$, $\sigma$ defines the ILS (or apodization), $K(\bar{v}_i)$ is the absorption coefficient of the species being observed and l is the pathlength through the sample. A conclusion drawn from the Griffiths paper is that this apodization induced distortion causes significant deviations from Beer's law when the true absorbance of a peak exceeds 0.7 AU.

The referenced literature also shows, and it can be inferred from Equation (1), that deviations from Beer's law are also a function of the instrument resolution relative to the narrowness of the spectral line being measured. A quantity called the resolution parameter, ρ, is defined as the ratio of the instrument resolution, R, to the full-width-half-height (FWHH) of the spectral band of interest as set forth by Equation (2):

$$\rho = R/FWHH \qquad \text{Eq. (2)}$$

The effect of ρ on photometric accuracy can be understood in the limit by examining Equation (1). If the ILS is thought of as a Dirac-delta or impulse function (i.e., perfect instrument resolution), then the ILS convolution in Equation (1) yields the absorbance term independent of ILS, in other words the true absorbance spectrum is measured if the instrument operates with infinite resolution. On the other hand, if the absorbance term is thought of as a delta function, we are left with only the ILS centered at the discrete wavelength where the absorption line occurs. One can then summarize from the referenced literature that photometric inaccuracy due to apodization is a function of both ρ and the spectral absorbance of the sample as set forth in Equation (3):

$$\text{Error} = f\{\rho, A^T(\bar{v})\} \qquad \text{Eq. (3)}$$

where $A^T(\bar{v})$ is the true absorbance of all absorbers in the sample.

It will be shown below that when there are different absorbers in the sample and background (for example, liquid water, glucose and water vapor in the sample and only water vapor in the background), the background will never capture a system perturbation in the same way that the sample will record the same perturbation. The strategy for using a background in spectroscopy is to capture and correct for instrumental or environmental variations so that the true absorbers in the sample can be identified. If the coefficients of absorption are included for all absorbers in the system, Equation (1) can be rewritten to represent the measured transmission of any sample in any environment. For the particular case of glucose in water in the presence of water vapor, Equation (1) becomes Equation (4):

$$T_s^A(\bar{v}_i) = \int_0^\infty \sigma(\bar{v} - \bar{v}_i) e^{-K_I(\bar{v})l_I} e^{-K_g(\bar{v})l_g} e^{-K_w(\bar{v})l_w} e^{-K_v(\bar{v})l_v} \quad \text{Eq. (4)}$$

where the subscript "I" represents instrument, "g" represents glucose, "w" represents liquid water and "v" represents water vapor present in the measuring environment. A typical background sample spectrum containing no glucose or water would be written as Equation (5):

$$T_b^A(\bar{v}_i) = \int_0^\infty \sigma(\bar{v} - \bar{v}_i) e^{-K_I(\bar{v})l_I} e^{-K_v(\bar{v})l_v} \quad \text{Eq. (5)}$$

where the background spectrum measures the instrument absorbance and the water vapor absorbance. The background corrected sample spectrum would be written as Equation (6):

$$\frac{T_s^A(\bar{v}_i)}{T_b^A(\bar{v}_i)} = \frac{\int_0^\infty \sigma(\bar{v} - \bar{v}_i) e^{-K_I(\bar{v})l_I} e^{-K_g(\bar{v})l_g} e^{-K_w(\bar{v})l_w} e^{-K_v(\bar{v})l_v}}{\int_0^\infty \sigma(\bar{v} - \bar{v}_i) e^{-K_I(\bar{v})l_I} e^{-K_v(\bar{v})l_v}} \quad \text{Eq. (6)}$$

As shown in Equation (1) the spectral intensity at each optical frequency depends on the spectral intensity of the adjacent frequencies measured by the instrument, the absorption terms for the instrument $e^{-K_i(\bar{v})_i l}$ and the water vapor $e^{-K_{vl}(\bar{v})_v l}$ do not cancel in Equation (6), resulting in a background corrected spectrum that is not equal to the true absorbance spectrum of the measured analytes. The only way these terms will ever cancel is if all other absorption terms that are not common to both sample and background are negligible or do not vary with optical frequency. Equation (6) can be expanded further to encompass any instrumental or environmental perturbation from the calibration state as set forth by Equation (7):

$$\frac{T_{s+\Delta}^A(\bar{v}_i)}{T_{b+\Delta}^A(\bar{v}_i)} = \frac{\int_0^\infty \sigma(\bar{v} - \bar{v}_i) e^{-K_I(\bar{v})l_I} e^{-K_g(\bar{v})l_g} e^{-K_w(\bar{v})l_w} e^{-K_v(\bar{v})l_v} e^{-K_\Delta(\bar{v})l_\Delta}}{\int_0^\infty \sigma(\bar{v} - \bar{v}_i) e^{-K_I(\bar{v})l_I} e^{-K_v(\bar{v})l_v} e^{-K_\Delta(\bar{v})l_\Delta}} \quad \text{Eq. (7)}$$

where the subscript $\Delta$ represents the absorption due to the perturbation. Maintenance of calibration could be achieved using any reference sample if the ratio in Equation (7) were equal to the ratio in Equation (6). However, as long as the unknown sample and reference sample have different spectral characteristics, Equation (7) will never identically equal Equation (6). The two equations become more similar as the reference sample begins to absorb more like the prediction sample.

In summary, a similar background is required when the system perturbation is not well modeled and the perturbation is not negligible in magnitude compared to the absorbers in the prediction sample, or when the spectral resolution (full width at half height) of the perturbation is much less than the instrument resolution. Another way to write this requirement is in terms of the final regression coefficients from a multivariate calibration model acting on the spectrum of the unknown sample. This can be written as Equation (8):

$$\vec{F} \cdot (\vec{S}_o + \vec{S}_{NL} + \vec{\varepsilon}) \Longrightarrow \vec{F} \cdot \vec{S}_{NL} << \vec{F} \cdot \vec{\varepsilon} \quad \text{Eq. (8)}$$

where $\vec{F}$ represents a vector of final regression coefficients, $\vec{S}_o$ represents the true spectrum, $\vec{S}_{NL}$ represents the distorted, or non-linear, part of the measured spectrum due to the finite resolution of the instrument and $\vec{\varepsilon}$ represents the spectral error due to sources of random error. In other words, the product of the final regression coefficients and the non-linear portion of the measured spectrum caused by a system perturbation should be much less than the product of the final regression coefficients and the random error present in the measured spectrum so that the error term due to the distorted part of the spectrum is small and prediction performance is maintained.

There are several different types of instrumental and environmental variation which may affect the prediction capability of a calibration model. It is possible, and highly desirable to reduce the magnitude of the effect of instrumental and environmental variation by incorporating this variation into the calibration model. It is difficult, however, to span the entire possible range of instrument states during the calibration period. System perturbations can result in the instrument being operated outside the space of the calibration model. Measurements made while the instrument is in an inadequately modeled state will exhibit prediction errors which render the measurement useless. In the case of in vivo optical measurements, these types of errors may result in erroneous medical information being used for the treatment of patients. These errors are obviously unacceptable in a commercial device.

Some examples of problematic instrument and environmental variation include, but are not limited to: changes in the levels of environmental interferents such as water vapor or $CO_2$ gas, changes in the alignment of the instrument's optical components, fluctuations in the output power of the instrument's illumination system, and changes in the spatial and angular distribution of the light output by the instrument's illumination system. It will be shown through both simulated and empirical results that a spectrally similar background sample provides improved capability to correct for these types of variations.

Correcting for any of the classes of instrument and environmental variation requires that the background sample have matched spectral absorption features with the sample of interest. It has already been shown mathematically that the finite instrument resolution causes the effect of different instrument states to depend on the spectral absorption characteristics of the sample (Equation (7)). Another way of stating this problem is that the optical effects of instrument and environmental variation should ideally be identical in both the background sample and the sample of interest. Taking the derivative of Equation (4) with respect to water vapor absorption yields Equation (9):

$$\frac{dT_s^A(\bar{v}_i)}{dK_v(\bar{v})} = \int_0^\infty -l_v \sigma(\bar{v} - \bar{v}_i) e^{-K_I(\bar{v})l_I} e^{-K_g(\bar{v})l_g} e^{-K_w(\bar{v})l_w} e^{-K_v(\bar{v})l_v} d\bar{v} \quad \text{Eq. (9)}$$

It is apparent from Equation (9) that the spectrum of water vapor is modified by the spectral shape of all compounds in the sample. This relationship holds true for any system perturbation which causes a change in the optical appearance of a sample's spectrum.

Simulated results are presented for the effects of water vapor level variation on the in vitro measurement of glucose in reflectance using scattering media. Actual spectra from 98 glucose solution samples were collected using an FTIR spectrometer operated at 16 cm$^{-1}$ resolution. The samples contained variable levels of scattering media to simulate optical pathlength distributions similar to those seen in living tissue. For comparison purposes, spectra from two different types of background samples were also collected: a similar background with matched optical properties and an air background (i.e. an integrating sphere placed over the reflectance sampler). High-resolution water vapor spectra (obtained at 1 cm$^{-1}$) were then artificially added to the solution and background spectra in order to simulate varying water vapor levels. Simulations were run on the resulting spectra in order to model the effects of finite instrument resolution on the added interferents. The sample spectra were then ratioed to the background sample spectra in an attempt to remove the effects of the varying water vapor levels. FIG. 1 shows the residual spectral effects after this background correction was performed. The two plots in FIG. 1 show the remaining spectral differences when the ratioed spectra with added water vapor are subtracted from the original ratioed spectra without added water vapor. As can be seen in the figure, the spectrally similar background reduces the effects of the water vapor interferent by a significant amount. A calibration developed at a constant water vapor was used to predict on the sample spectra. As stated above, the sample spectra were ratioed against a similar background with matched optical properties and an air background. The prediction errors for the sample data with the air background ratio were inflated over the sample spectra with a similar background by approximately 40 mg/dl using a calibration model with 20 factors. This simulation clearly demonstrates the advantage of using a similar background for correcting for even simple system perturbations.

Many of the types of instrument variation involve interactions with the sampling geometry of the sample. These types of instrument variation include changes in alignment of optical components and changes in angular and spatial distribution of the output light from the instrument's illumination system. These types of variations may be caused by a number of physical mechanisms, including: aging of optical mounts, thermally induced mechanical deformations of optical mounts, aging of light sources, or variations in routinely replaced components such as light bulbs. In order to be effective, the background sample must preserve the same mapping of angular and spatial distribution of light as the sample of interest. This requires that the background sample interact with the sampling optics of the instrument in a manner that mimics the interaction of the sampling optics with the sample of interest.

An additional constraint which is generally required for successful calibration maintenance is that the overall intensity of light seen at the optical detector elements be closely matched for both the background sample and the sample of interest. This constraint helps to correct for non-linearities in the instrument's optical measurement characteristics. Again, this constraint is included in the overall definition of similar spectral radiance.

Figure 2:
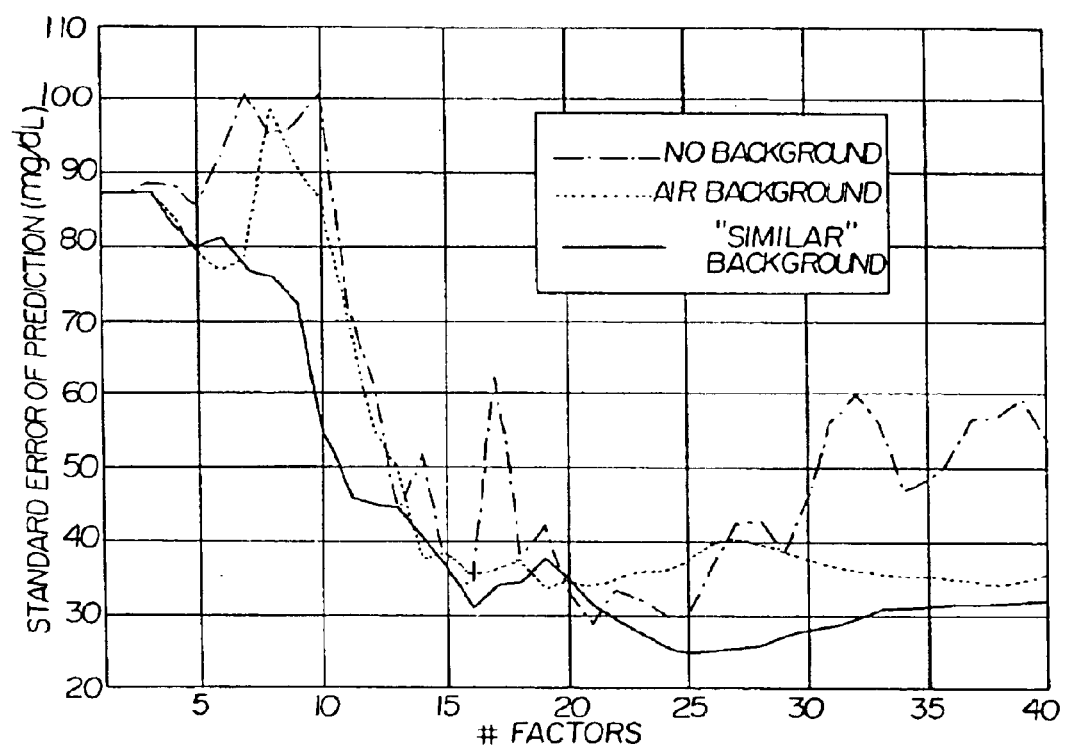
FIG. 2 shows a graph of standard error of prediction comparing no background, a conventional air background, and a similar background in accordance with the present invention in the presence of instrument and environmental variation.
Figure 3:
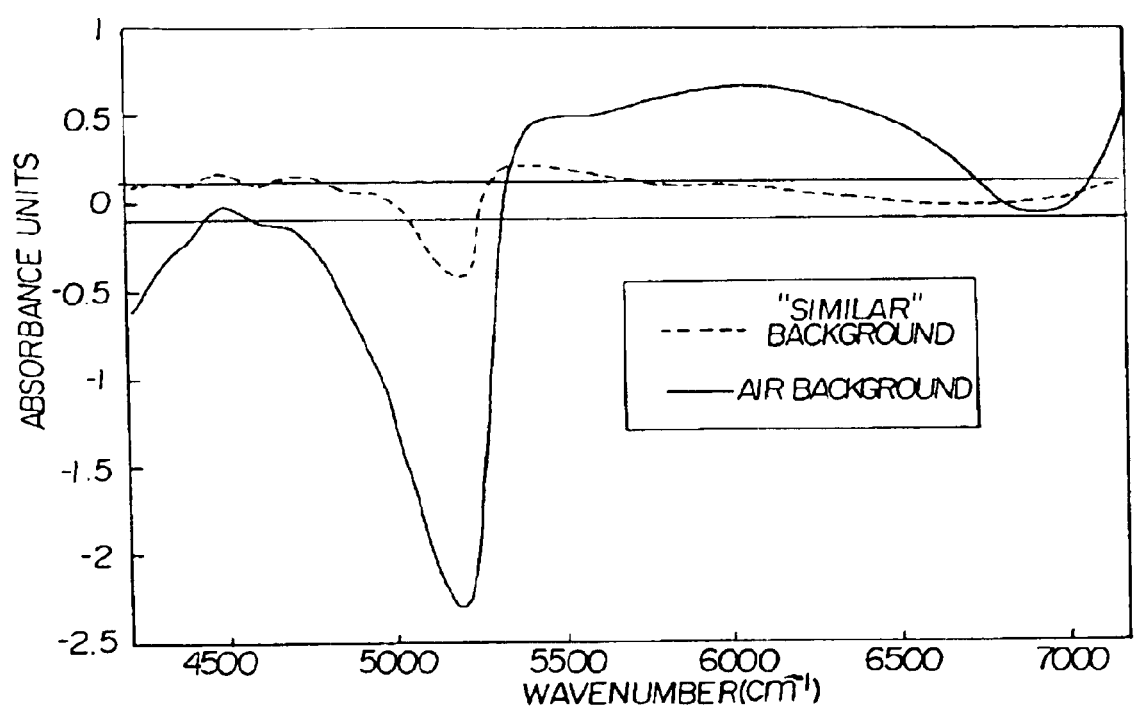
FIG. 3 shows a graph of the spectral differences between the mean human tissue spectrum and two different backgrounds, namely a conventional air background and a similar background in accordance with the present invention.

Empirical results are presented for an actual, in vivo study measuring blood glucose concentrations non-invasively. The study was intentionally designed to include several of the types of instrument and environmental variation previously discussed herein. Specifically, ambient relative humidity, ambient temperature, and illumination power were all varied during the prediction phase of the study. This study was intended as a proof of concept for using a similar background reference sample for calibration maintenance. The study was limited to five subjects over a period of two days. Prediction errors were determined by comparing non-invasive results to standard capillary blood glucose reference measurements. FIG. 2 demonstrates the superior ability of the similar background to maintain the prediction performance of the calibration in the presence of instrument and environmental variation by generating a lower standard error of prediction and by generating the smoothest decreasing SEP curve. FIG. 3 shows the spectral differences between the mean human tissue spectrum and the two different background sample types being tested in the study.

Figure 4:
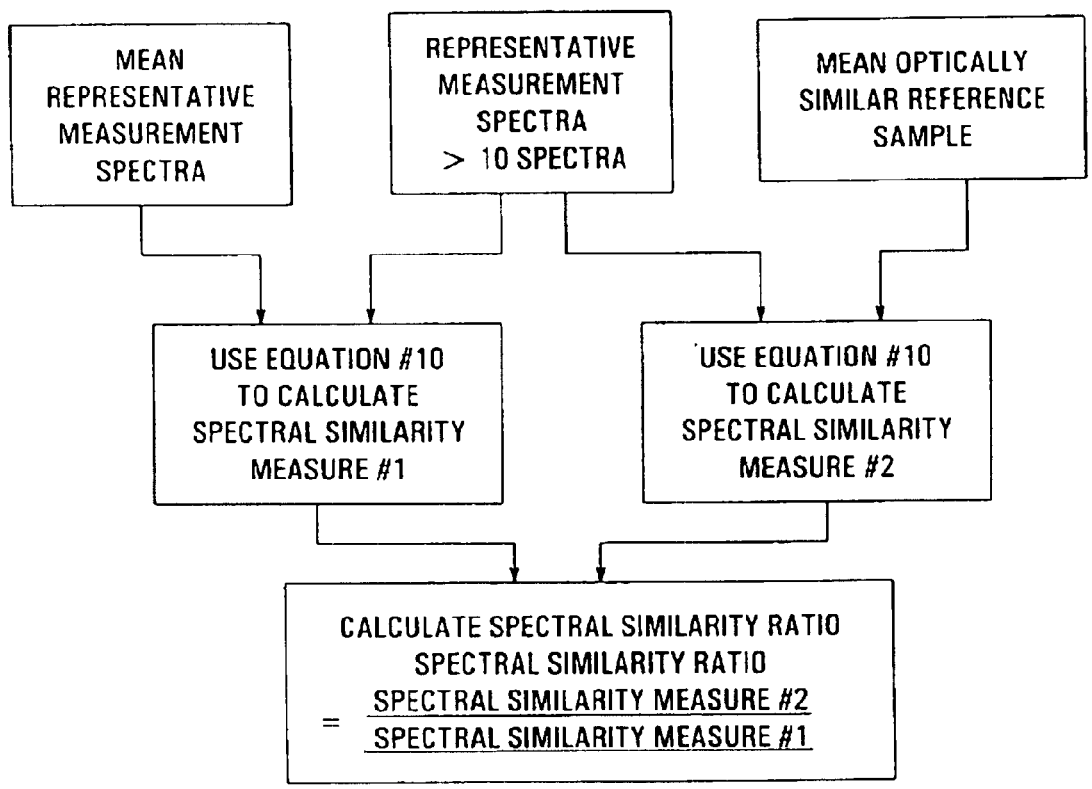
FIG. 4 is a flowchart illustrating the steps used in quantifying spectral similarity.

Refer now to FIG. 4 which illustrates a flowchart for determining spectral similarity, while FIGS. 5–21 show various embodiments of optically similar reference samples of the present invention, and show various graphs demonstrating the improved performance with the use of an optically similar reference sample. Each optically similar reference sample discussed with reference to FIGS. 5–21 basically provides a background that has a spectrum that is similar to the test sample. In other words, the similar background absorbs the same or similar intensity of light at each wavelength over the range of selected relevant wavelengths measured.

The spectral similarity of an optically similar reference sample to the test sample of interest may be quantified with respect to spectral absorbance, mapping of input to output light spatial distribution, and mapping of input to output light angular distribution.

There are two metrics that may be used to calculate the similarity of a particular background sample to the sample of interest with respect to spectral absorbance. The first involves comparing the optically similar reference sample in question to the test samples, typically tissue spectra, where all of the background and tissue spectra were collected near in time, as set forth in Equation 10:

$$\text{Spectral Similarity} = \frac{\sum_{i=1}^{I}\left(\sum_{j=1}^{J}(X_{ij}-z_i)^2\right)}{I} \quad \text{Eq. (10)}$$

where X is a set of tissue pseudo-absorbance spectra and z is any mean background pseudo-absorbance spectrum for the time in question. (The pseudo-absorbance spectrum is defined in Equation 11). I refers to the total number of data points collected in the wavelength region of interest (or the total number of discrete wavelengths chosen for analysis), and J refers to the total number of tissue spectra collected in this period of time. The average value of the spectrum should be subtracted from all wavelengths before calculating the metrics. This step ensures that the spectral shapes of the background and tissue are correctly compared without being influenced by a uniform, DC energy offset or baseline shift.

$$\text{Pseudo-}absorbance = -\log_{10}(I) \quad \text{Eq. (11)}$$

where I is a single beam intensity spectrum.

Quantifying the degree of spectral similarity can be done through a straightforward process involving a comparison between the spectra in which the analyte is to be measured and the optically similar reference sample. The flowchart of FIG. 4 summarizes this process. The process involves the following steps:

Step 1: Define or establish the representative measurement sample. A representative measurement sample is a sample that is representative of samples on which the optical measurement system will be making subsequent measurements. If the application is a single patient with diabetes, then a representative measurement sample would be a sample at the sampling location on that patient. If the application group is a heterogeneous group of subjects, then the representative measurement samples would be an appropriate group of subjects on which the monitor would be subsequently used. If the measurement group were other sub-populations of subjects, then the representative measurement samples would be obtained from the sub-population. For example, in patients with renal disease, the representative measurement population would be patients with renal disease.

Step 2: Obtain spectral measurements from the representative measurement samples. In all cases, multiple measurements with reinsertion of the tissue into the sampling device should be made. In the case of a single subject application, at least ten spectral measurements should be made. In the case of a heterogeneous patient population, the representative measurement samples should be a reflection of the subjects that will subsequently use the monitor. In the example below, 30 subjects of varying ages, gender, ethnicity and body mass index were used. The spectral measurements should be made in a manner consistent with use of the monitoring device. These spectra are hereafter referred to as the representative measurement spectra.

Step 3: Calculate a mean pseudo-absorbance spectrum from the spectra obtained from the representative measurement samples. The resulting spectrum is hereafter referred to as the mean representative measurement spectrum.

Step 4: Obtain spectral measurements from the optically similar reference sample. In all cases, multiple insertions and measurements of the optically similar reference sample should be made. It is preferred that at least 10 measurements should be made. These spectra are hereafter referred to as the optically similar reference sample spectra.

Step 5: Calculate a mean pseudo-absorbance spectrum from the optically similar reference sample spectra. The resulting spectrum is hereafter referred to as the mean optically similar reference spectrum.

Step 6: Use the representative measurement spectra and the mean representative measurement spectrum with Equation #10 to calculate a spectral similarity value. The resulting value will hereafter be referred to as the spectral similarity measure #1.

Step 7: Use the representative measurement spectra and the mean optically similar reference spectrum with Equation (10) to calculate a spectral similarity value. The resulting value will hereafter be referred to as the spectral similarity measure #2.

Step 8: Ratio the two spectral similarity values to obtain a spectral similarity ration. Spectral similarity ratio=

$$\frac{\text{Spectral Similarity Measure \#2}}{\text{Spectral Similarity Measure \#1}}$$

Equation (10) is a mean sum of squares metric, and it may be calculated for different wavelength regions. It may be calculated for a continuous spectral region, for discrete wavelengths, for combinations of two or more discrete wavelengths (which may or may not have been found using a wavelength or variable selection algorithm), or for selected regions of a spectrum.

Table 1 below shows the values that were calculated for Equation (10) for a representative group of subjects for three levels of similarity: acceptable, preferred, and ideal. The spectral regions and discrete wavelengths for which these values were calculated are also indicated in the table. The discrete variables used in this case are glucose-important wavelengths (listed by wavenumber in $cm^{-1}$) and are specified in Table 2. The more similar the background is to the tissue spectra, the smaller the Spectral Similarity value becomes. Table 3 shows the same spectral similarity metrics when the representative sample is a single subject.

TABLE 1

| | | Spectral Similarity Ratio | | |
| --- | --- | --- | --- | --- |
| Level of Similarity | Example Background Sample | Full Spectrum ($4,200\ cm^{-1}$–$7,200\ cm^{-1}$) | Discrete Variables | Absorbance Troughs ($4,440\ cm^{-1}$–$4,800\ cm^{-1}$ & $5,400\ cm^{-1}$–$6,400\ cm^{-1}$) |
| Acceptable | Scattering Solutions | 30 | 30 | 30 |
| Preferred | Transmission Cell | 10 | 10 | 10 |
| Ideal | Mean Subject Spectrum | 1 | 1 | 1 |

TABLE 2

Glucose-important variables used in spectral similarity calculations

| | | | | | | |
| --- | --- | --- | --- | --- | --- | --- |
| 4196 | 4451 | 4883 | 5369 | 5731 | 6163 | 6696 |
| 4227 | 4459 | 4922 | 5392 | 5755 | 6187 | 6935 |
| 4273 | 4497 | 5014 | 5454 | 5785 | 6287 | 6973 |
| 4281 | 4528 | 5091 | 5469 | 5809 | 6318 | 7004 |
| 4304 | 4559 | 5176 | 5477 | 5839 | 6349 | 7043 |
| 4320 | 4613 | 5230 | 5515 | 5893 | 6449 | 7066 |
| 4335 | 4690 | 5269 | 5585 | 5924 | 6472 | 7205 |
| 4366 | 4775 | 5299 | 5623 | 5947 | 6557 | |
| 4389 | 4829 | 5315 | 5662 | 6001 | 6595 | |
| 4436 | 4860 | 5338 | 5701 | 6094 | 6673 | |

TABLE 3

| Level of Similarity | Example Background Sample | Spectral Similarity Ratio | | |
|---|---|---|---|---|
| | | Full Spectrum (4,200 cm$^{-1}$–7,200 cm$^{-1}$) | Discrete Variables | Absorbance Troughs (4,440 cm$^{-1}$–4,800 cm$^{-1}$ & 5,400 cm$^{-1}$–6,400 cm$^{-1}$) |
| Acceptable | Scattering Solutions | 1500 | 1500 | 7500 |
| Preferred | Transmission Cell | 1000 | 1000 | 2500 |
| Ideal | Mean Subject Spectrum | 1 | 1 | 1 |

If an analyte is to be determined, it is helpful if the background matches different regions and/or discrete wavelengths of the spectrum that are important in the determination. In other words, if spectral region A is important in determining the analyte, then the background should match the tissue especially well in region A. On the other hand, region A may not be at all important in determining a different analyte, in which case the spectral match would be less important for that region. When an analyte is to be determined, therefore, another metric must also be defined that is specific to the analyte in question, as shown in Equation (12) below.

$$\text{Regression weighted Similarity} = \frac{\sum_{i=1}^{I}\left(\sum_{j=1}^{J}(b_i * X_{ij} - b_i * z_i)^2\right)}{I} \quad \text{Eq. (12)}$$

where b is the regression vector for the analyte being determined, normalized to length one, and the other symbols have the same meanings as in Equations (10) and (11). This regression vector may be calculated via any linear or non-linear regression method, where partial least squares is an example of such a method. It may be thought of as the analyte's calibration model, and it weights the absorbances at different wavelengths based on their importance in predicting the analyte characteristic of interest.

The process for quantifying the degree of spectral match is the same except that Equation (12) is used instead of Equation (10). The 8-step process is the same with a single substitution of the equations. The resulting ratio will hereafter be referred to as the regression weighted spectral similarity ratio.

Table 4 shows results from Equation (12), calculated for a representative group of subjects when the analyte of interest was glucose; however, these values may also be calculated for any component in the sample that is to be determined. It can be seen that the ideal background has a much smaller Spectral Similarity value than the acceptable background, since it is more similar to tissue spectra collected during the same period of time. The more similar the background is, the smaller the Spectral Similarity value will be for Equation (10) or Equation (12) or both, for any spectral region or any combination of regions or any discrete wavelength or combination of discrete wavelengths. Table 5 shows the same spectral similarity metrics when the representative sample is an individual subject. In an analysis where no specific characteristic (e.g. concentration) of the sample is being measured, then Equation (10) is sufficient. When a specific characteristic is to be determined, however, both Equations (10) and (12) may be evaluated.

If the spectral similarity ratio for the optically similar reference sample value is less than 30, then the optically similar reference sample is to be considered an acceptable optically similar reference sample. If the spectral similarity ratio is less than 10, then the optically similar reference sample is to be considered a preferred optically similar reference sample. If the spectral similarity ratio is less than or equal to 1, then the optically similar reference sample is to be considered an ideal optically similar reference sample. The metrics must be calculated for the analyte being determined and for the wavelengths/wavelength regions being used to ensure the validity of the similarity determination.

TABLE 4

| Level of Similarity | Example Background Sample | Regression Weighted Spectral Similarity Ratio | | |
|---|---|---|---|---|
| | | Full Spectrum (4,200 cm$^{-1}$–7,200 cm$^{-1}$) | Discrete Variables | Absorbance Troughs (4,440 cm$^{-1}$–4,800 cm$^{-1}$ & 5,400 cm$^{-1}$–6,400 cm$^{-1}$) |
| Acceptable | Scattering Solutions | 30 | 30 | 30 |
| Preferred | Transmission Cell | 10 | 10 | 10 |
| Ideal | Mean Subject Spectrum | 1 | 1 | 1 |

TABLE 5

| | | Regression Weighted Spectral Similarity Ratio | | |
|---|---|---|---|---|
| Level of Similarity | Example Background Sample | Full Spectrum (4,200 cm$^{-1}$–7,200 cm$^{-1}$) | Discrete Variables | Absorbance Troughs (4,440 cm$^{-1}$–4,800 cm$^{-1}$ & 5,400 cm$^{-1}$–6,400 cm$^{-1}$) |
| Acceptable | Scattering Solutions | 4500 | 3000 | 9000 |
| Preferred | Transmission Cell | 1500 | 2500 | 3000 |
| Ideal | Mean Subject Spectrum | 1 | 1 | 1 |

The similarity of the mapping function of light spatial distribution and light angular distribution can also be quantified for optically similar reference samples. The preferred method for quantifying the similarity of these properties is to examine the image of the output light beam, which is produced after the light, has passed through the sampling optics and the sample of interest. For purposes of this discussion, the light beam is assumed to be circular in cross-section, but the similarity metrics can be extended to any geometry of beam (e.g. the output of a square cross-section light guide). The boundary of the light beam passing through the sample is defined as the points at which the light intensity falls to $1/e^2$ times the peak light intensity.

The image of the output beam is measured using any standard intensity mapping scheme (e.g. scanning a single pixel detector or using a CCD camera) and using a goniometer. This allows both the spatial and angular distributions of the light beam to be determined. Measurements should be made for both the sample of interest and for the similar background being quantified. In order to standardize the calculation for many applications, the image should be divided into approximately one hundred equally sized "bins" (or squares), with ten bins across the diameter of the image. This can be accomplished by either measuring the beam in a ten by ten grid or by sampling at a finer spacing and then averaging the data. The spatial and angular distributions for the sample of interest are then subtracted from the corresponding distributions of the background sample. The resulting images represent the similarity level for the background and the sample of interest. In order to quantify this similarity, all of the data points in the image are put into a vector for easier calculation, and the vector is normalized so that its length equals 1. This is achieved by dividing each data point in the image by the 2-norm $(\|x\|_2)$, which is equivalent to the Euclidean distance of the vector.

$$\|x\|_2 = \left(\sum_{i=1}^{n} |x_i|^2\right)^{1/2} \quad \text{Eq. (13)}$$

where x is the vector of the difference image and n is the number of data points in that vector.

The normalization step ensures that the magnitude of every difference-image is comparable. Following the normalization step, the standard deviation of the normalized image vector is calculated, and this metric is an indication of how similar the background and sample images are. Table 6 shows the standard deviations that are ideal, preferred and acceptable for the spatial distribution of similar backgrounds. Table 7 shows the same metrics for angular distribution.

TABLE 6

| Level of Similarity | Spatial Similarity Metric (Standard Deviatio) |
|---|---|
| Acceptable | 0.079 |
| Preferred | 0.052 |
| Ideal | 0 |

TABLE 7

| Level of Similarity | Angular Similarity Metric (Standard Deviation) |
|---|---|
| Acceptable | 0.051 |
| Preferred | 0.036 |
| Ideal | 0 |

As stated previously, the optically similar reference sample is used to capture the current instrument state such that the effect of instrumental and environmental variation on prediction capability can be eliminated. There are several different methodologies by which the reference spectrum can be used to correct for instrumental and environmental variation. These spectral correction methods include, but are not limited to those described below.

These correction methodologies can be classed into two broad categories: methods which modify the spectrum of the test sample and methods which modify the calibration model. The simplest and preferred method modifies the spectrum of the sample of interest by subtracting the optically similar reference spectrum in absorbance space. The reference spectrum may be the most recently collected optically similar reference spectrum, or it may be an averaged spectrum containing information from several background samples collected at different points in time. One preferred method of averaging is to exponentially time weight the background reference spectra and average them together. The exponentially time weighted method allows for the optimization of achieving high signal-to-noise-ratio correction data and capturing the current instrument state.

The second class of background correction methodologies consists of actually modifying the multivariate calibration model. One simple method is to simply include the reference spectra with the original calibration samples and rerun the regression algorithm on the combined data set. A preferred method is to include only the spectral variation from the background reference sample in the calibration model. This method consists of taking multiple background reference samples during the calibration period, finding the mean of the background reference sample spectra collected during the calibration period, subtracting (in absorbance space) this mean background reference spectrum from subsequent background reference spectra collected prior to making an actual prediction, adding this spectral difference back to the calibration samples, and rerunning the regression algorithm to create an updated calibration model. In an alternative method, an eigenvector decomposition is run on the spectral differences seen in the background and a limited number of eigenvectors is used to add this spectral variation back to the model.

Each of the similar background embodiments discussed with reference to FIGS. 5–21 may be used in combination with an infrared spectrometer 10 having an illumination source 12 and a collection system 14 as disclosed in U.S. Pat. No. 4,975,581 to Robinson et al., entitled "Method of and Apparatus for Determining the Similarity of a Biological Analyte from a Model Constructed from Known Biological Fluids", the entire disclosure of which is hereby incorporated by reference. Also, each of the similar background embodiments may be used in combination with a calibration model (not shown), a suitable example of which is disclosed in U.S. Pat. No. 6,157,041, entitled "Methods and Apparatus for Tailoring Spectroscopic Calibration Models", the entire disclosure of which is hereby incorporated by reference.

Detailed descriptions of several specific embodiments of the present invention are provided below with reference to FIGS. 5–21. These specific backgrounds are intended for applications in which analyte concentrations are to be measured in vivo using reflection spectroscopy. Specifically, these optically similar reference samples are designed to match the optical properties of tissue at selected wavelengths in the near-infrared region including 4,000 cm$^{-1}$ to 8,000 cm$^{-1}$. In this optical region, water is the dominant absorbing component contained in the tissue. Each of the following backgrounds is designed to provide multiple optical pathlengths through water in order to mimic the spectrum of living tissue. Based upon Monte Carlo simulations of light propagation through scattering media where the scattering properties match those of tissue, a distribution of pathlengths can be calculated. The results can be defined by a mean pathlength with a standard deviation and skew to the distribution. The distribution skew is toward longer pathlengths. Typically the standard is less than or equal to the mean. For example, if the mean pathlength is 1 mm, then the standard deviation of pathlengths is about 1 mm as well.

In developing and assessing reference samples, is important to have a metric that enables one to rapidly and easily determine if multiple optical pathlengths of water are created by the reference sample. One simple way is to fit the absorbance spectrum of the reference sample with three terms: 1) an offset, 2) a slope with wavenumber, and 3) the pure component of water. The pure component of water is simply the absorbance of water at a fixed pathlength. Mathematically stated:

$$\hat{A}(x)=b_0+b_1 x+b_2 PC(x) \quad \text{Eq. (14)}$$

The three fitting parameters are estimated using a least squares fit of the above equation to the absorbance spectrum (which has no instrument line shape in it). Following fitting of the above parameters the spectral residual is determined. The spectral residual is determined by subtracting the above equation from the absorbance spectrum of the reference sample. The final step is to compute the root-mean-squared (RMS) error across the spectrum.

$$\text{Multipath\_RMSError}=\sqrt{\frac{1}{N}\sum_{i=1}^{N}(A_i-\hat{A}_i)^2} \quad \text{Eq. (15)}$$

The multipath RMS error is greater when multiple pathlengths of water are present in the reference sample. A single pathlength sample will results in a smaller RMS error then a two pathlength sample, etc. A simple threshold value calculated in absorbance units can be used to determine if multiple pathlength of water are present. The threshold is sensitive to the spectral region used. For, example the threshold would be smaller if the region used for analysis had smaller absorbance bands.

Several novel designs are presented for achieving the multiple water pathlengths required to match the spectrum of tissue. Most embodiments consist of an optical interface (e.g., an MgF$_2$ window) which is highly transmissive in the optical region of interest, an optical sampling compartment containing water, and diffusely reflective or scattering media. For each background design, either experimental or simulated data are presented showing how close a spectral match was achieved between the background and human tissue.

These background designs are examples of embodiments of similar backgrounds for the specific application of measuring in vivo analyte concentrations in a particular optical region. Other optical regions or in vitro applications will require substantially different background embodiments.

The inventors recognize that in addition to including the dominant absorbing species (e.g., water), the background sample may also include the actual analyte of interest (e.g., glucose, ethanol, urea, etc.). By including various analytes, the background sample may be used as a quality control or calibration sample in addition to its primary use in the maintenance of calibration.

With specific reference now to FIGS. 5 and 6, a cone background device 100 is illustrated in accordance with an embodiment of the present invention. FIG. 5 illustrates representative ray-traces in the cone background device 100 and FIG. 6 illustrates a partial cut-away view of the cone background device 100. Cone background device 100 utilizes a conical geometry in order to help achieve some of the required performance specifications for a background similar to human tissue. It includes an optically transparent cone 130 such as a fused silica cone, a thin layer of a constituent 120 such as water, collagen or lipid, and a diffusing cone 110 which provides approximately Lambertian reflection of the incident radiation.

The cone geometry of device 100 provides excellent stray signal suppression as best seen in the ray trace shown in FIG. 5. The useful signal is transmitted through the hollow portion 140 of the cone, and then through the constituent layer 120. The amplitude of the signal that is reflected back to the collection system without undergoing the desired interaction is reduced significantly due to several Fresnel reflection losses. The useful radiation undergoes a randomized reflection from the diffusing cone 110 surface, and passes back into the inner cone volume 140, either to be collected or to undergo yet another pass through constituent layer 120 and random reflection. FIG. 7 shows a graph of spectral response demonstrating the spectral match between the tissue sample and the cone device 100.

The cone reference sample as designed contains a distribution of optical pathlengths through water. This distribution of water pathlengths was confirmed by calculating the multipath RMS error in the manner explained above. The multipath RMS error was calculated over the region of 4200–7200 cm$^{-1}$ and generated a value of 0.18 absorbance units.

Figure 8:
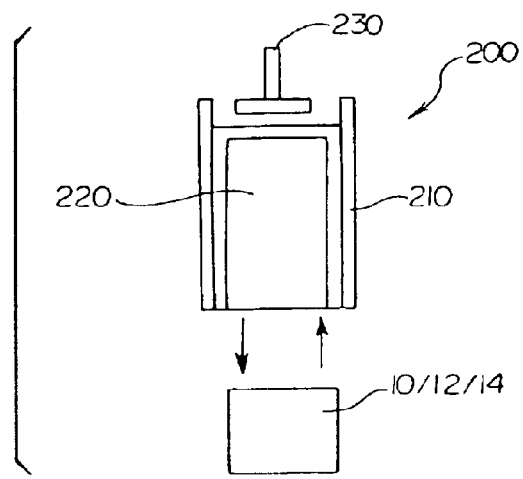
FIG. 8 schematically illustrates a scattering solution background in accordance with an embodiment of the present invention.
Figure 9:
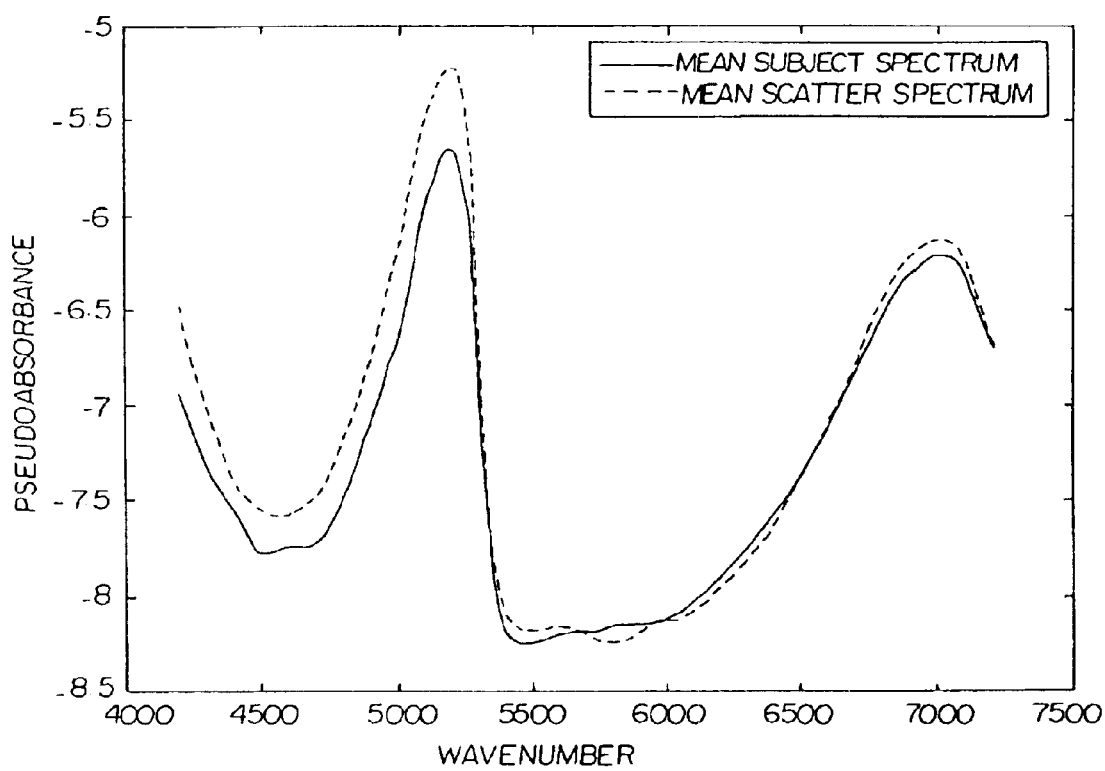
FIG. 9 shows a graph of spectral response demonstrating the spectral match between the tissue sample and the scattering solution background.

Refer now to FIG. 8, which schematically illustrates a scattering solution background device 200 in accordance with another embodiment of the present invention. The scattering solution background 200 includes a container 210 that is at least partially optically transparent adjacent the illumination source 12 and collection system 14. The scattering solution background also includes a scattering solution 220. Scattering solution 220 comprises a plurality of reflective beads disposed in a liquid or gel constituent such as water, collagen or lipid. The random pathlength distribution of the scattering solution 220 is provided by the reflective beads, which may comprise, for example, reflecting polystyrene microbeads (0.298 μm diameter, 6600 mg/dl concentration) in aqueous solution. The particle reflectance, size and concentration of the reflective beads in the scattering solution 220 are set in order to create the desired match to tissue for the solution 220. Preferably, the solution 220 is mechanically agitated by agitator 230 in order to prevent settling of the reflective beads. FIG. 9 shows a graph of spectral response demonstrating the spectral match between the tissue sample and the scattering solution background 200.

Figure 10A:
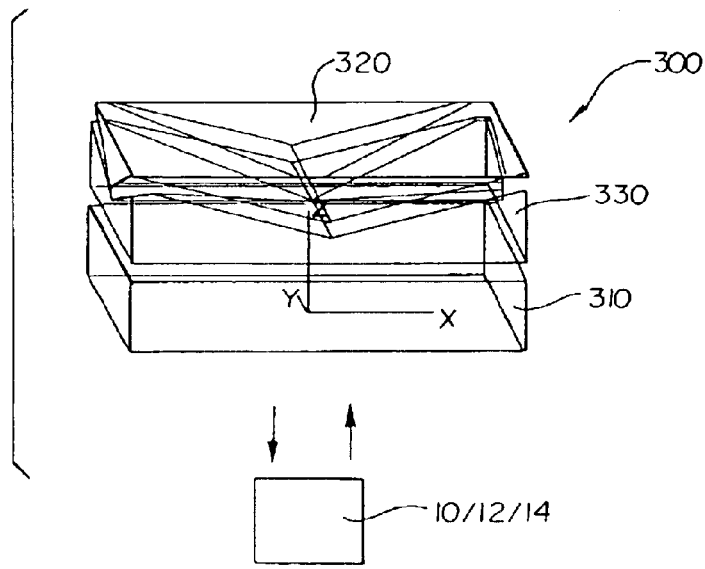
FIG. 10A schematically illustrates a roof background in accordance with an embodiment of the present invention.
Figure 10B:
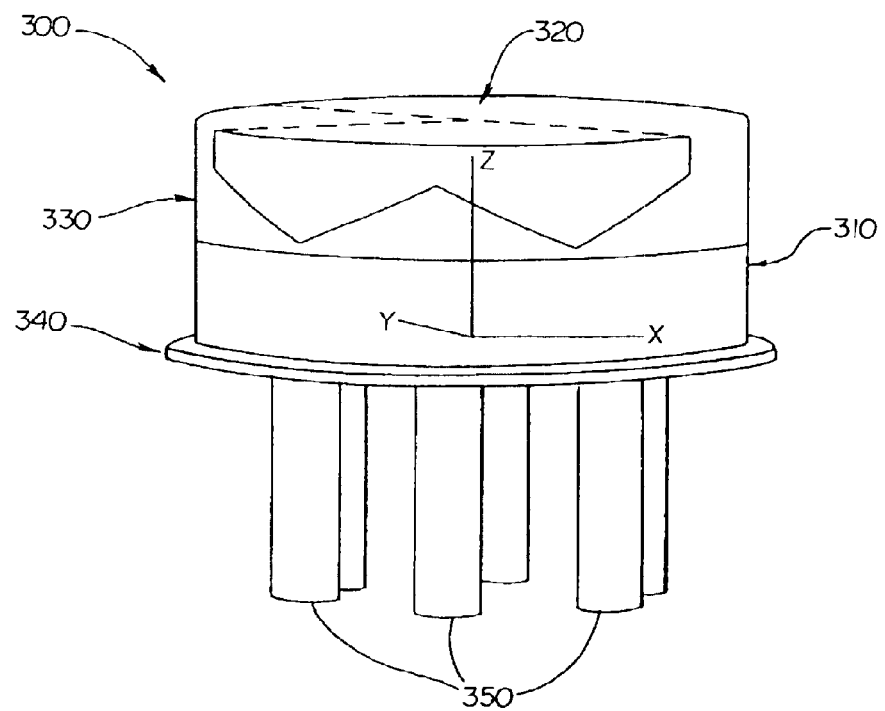
FIG. 10B schematically illustrates an alternative roof background as positioned on a fiber optic sampling array.

Refer now to FIGS. 10A and 10B, which schematically illustrate alternative, roof background devices 300 in accordance with yet another embodiment of the present invention. The roof background devices 300 make use of an optically transparent layer 310 such as a flat window comprising fused silica or MgF$_2$, a roof-like reflective diffuser 320, and a constituent layer 330 disposed therebetween. The optically transparent layer 310 may be used to surround and contain the constituent layer 330. The constituent layer 330 may comprise water, collagen, lipid, or a mixture thereof. The diffuser 320 may include an irregular or otherwise non-planar surface such as roughened aluminum or stainless steel, or Spectralon of the proper reflecting characteristics. Light passes from the illumination source 12 through the window 310 and constituent layer 330 to the diffuser 320. After undergoing a random reflection from the diffusing surface, the light passes back through the constituent layer 330 through the window 310 to the collection system 14. FIG. 10B further illustrates the roof background device 300 disposed on a sampler interface 340 to which a cluster of fiber optic bundles 350 is joined. Each fiber optic bundle preferably includes an arrangement of a plurality of input and output fiber optic cables.

Figure 11:
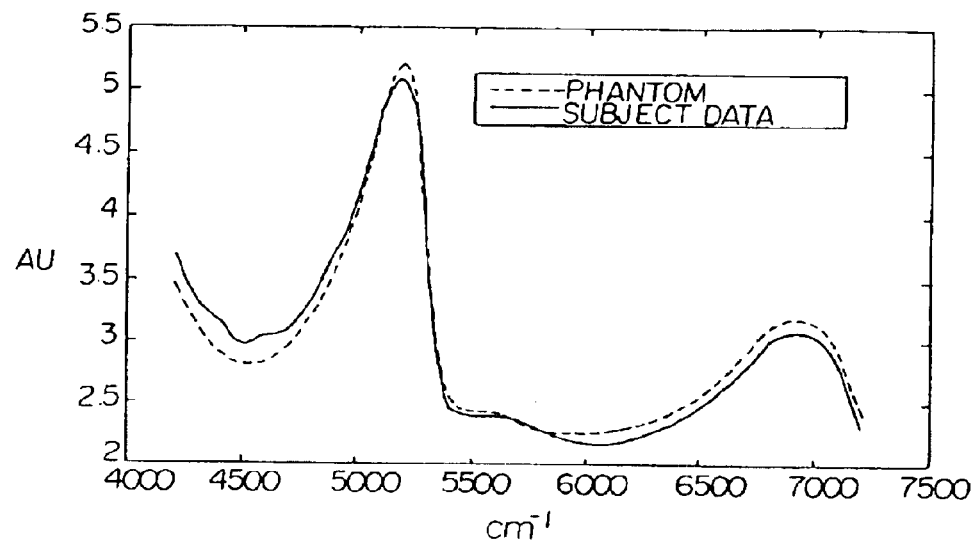
FIG. 11 shows a graph of spectral response demonstrating the spectral match between the tissue sample and the roof background.

The parameters of the device 300 may be adjusted so that the collected light has similar spectral radiance to light that has interacted with tissue. FIG. 11 shows a graph of spectral response demonstrating the spectral match between the tissue sample and the roof background 300. The angles of the diffusing surface and the thickness of the water path were adjusted in simulation to achieve the theoretical result shown in FIG. 11. The spectral response of this system was calculated from the pathlength distribution and the known absorption spectrum of water. It is important to note that the spectral match shown depends on adjusting the mean energy of the background to match that of tissue.

Figure 12:
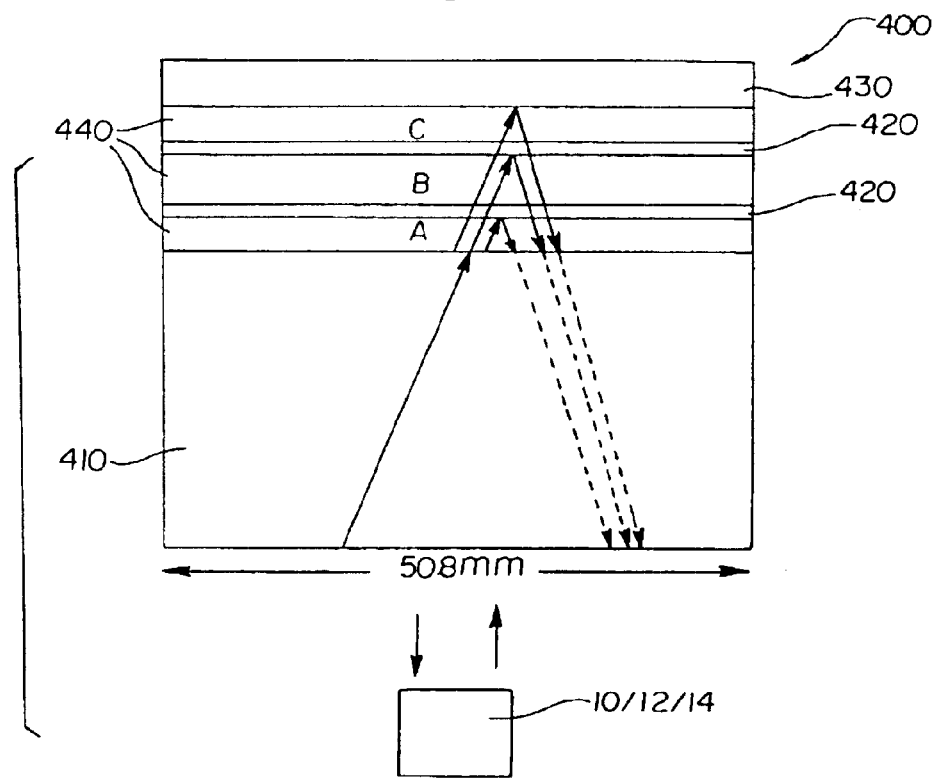
FIG. 12 schematically illustrates a multi-layer background in accordance with an embodiment of the present invention.

Refer now to FIG. 12, which schematically illustrates a multi-layer background device 400 in accordance with a further embodiment of the present invention. The multi-layer background device 400 is based on a match at discrete pathlengths to tissue. The multi-layer device 400 includes an optically transparent window 410 such as an MgF$_2$ window, a plurality of optical splitting layers 420 such as partially reflecting quartz microslides, and a reflecting layer or surface 430 such as a gold mirror. Multiple constituent layers 440, such as water, are disposed between the window, 410, the optically transparent layers 420, and the reflective layer 430. The optically transparent window 410 may be used to surround and contain the constituent layers 440. The diameter of the multi-layer background 400 is chosen to match the output area of the sampling optics for a given device.

Figure 13:
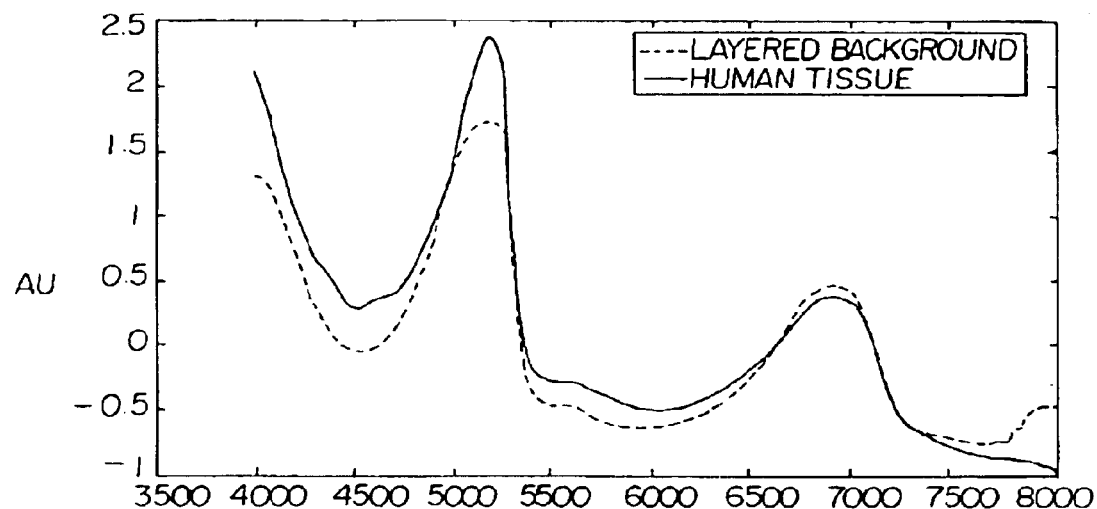
FIG. 13 shows a graph of spectral response demonstrating the spectral match between the tissue sample and the multi-layered background.

Incident light from the illumination source 12 is broken up into components with discrete pathlengths by the optical splitting layers 420. The reflectance of the optical splitting layers 420 and the thickness of the constituent layers 440 may be adjusted in order to achieve the proper distribution of pathlengths in the device 400 so that a match to tissue is achieved. FIG. 13 shows a graph of spectral response demonstrating the spectral match between the tissue sample and the multi-layered background 400. For this test, the water layers 440 (labeled A, B, and C) were sized as follows: A=170 μm, B=205 μm, and C=150 μm. The microslide 420 between layer A and B had 4% reflectance, and the microslide 420 between layer B and C had 32% reflectance. The gold mirror 430 had approximately 99% reflectance in the specified wavelength region.

Figure 14:
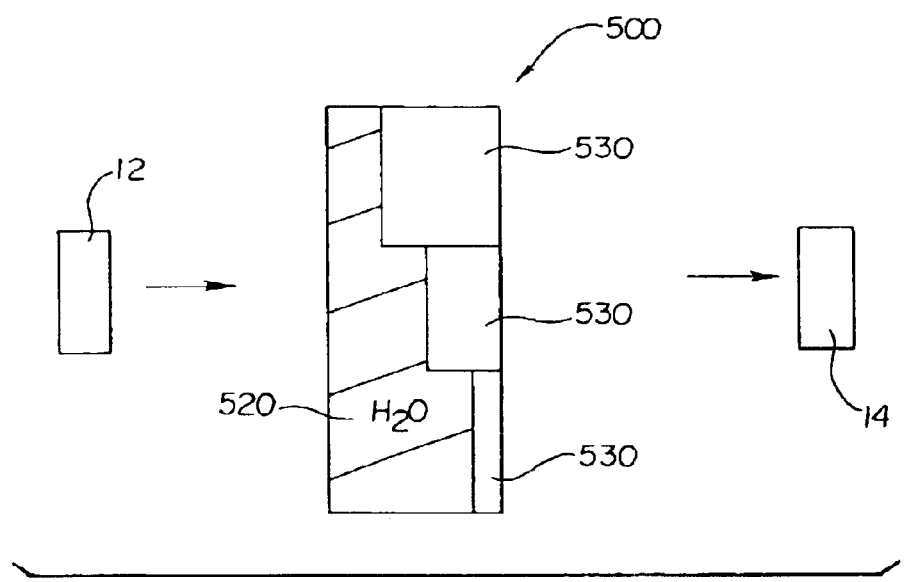
FIG. 14 schematically illustrates a transmission cell background in accordance with an embodiment of the present invention.
Figure 15:
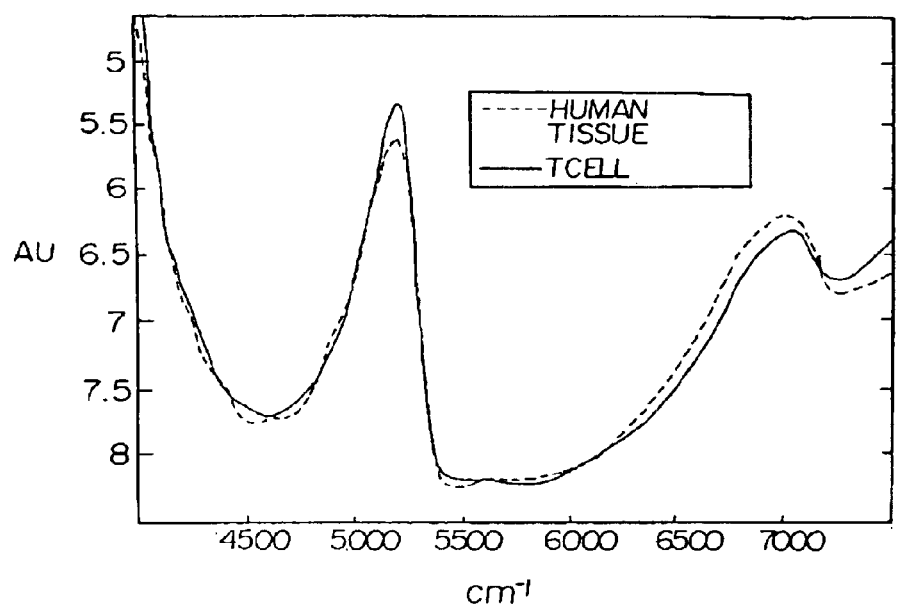
FIG. 15 shows a graph of spectral response demonstrating the spectral match between the tissue sample and the transmission cell background.

Refer now to FIG. 14, which schematically illustrates a transmission cell background device 500 in accordance with yet a further embodiment of the present invention. The transmission cell background device 500 also makes use of discrete constituent 520 pathlengths to match the pathlength distribution of tissue at key points. The transmission cell background device 400 includes an optically transparent container 510 such as fused silica windows containing a plurality of spacers 530 such as MgF$_2$ spacers to provide desired pathlengths. The remainder of the container 510 is filled with a constituent 520 such as water. The spacers function to displace the water or other constituent, creating a background with several different length water paths. Suitable dimensions for the cell spacers are 0.226", 0.216", and 0.197" respectively. These spacers may be used to create three water layers with thickness values of 0.0098", 0.0197", and 0.0393". The diameter of the transmission cell 400 is chosen to match the output area of the sampling optics for a given device. FIG. 15 shows a graph of spectral response demonstrating the spectral match between the tissue sample and the transmission cell background 400. FIG. 15 indicates the degree of match between the transmission cell (T-Cell) background 400 and the tissue sample to be on the order of +/−0.1 absorbance units.

The transmission cell background 400 may be incorporated into a transmission spectroscopy device by incorporating a second, reflective element (not shown). The transmission cell described above is placed into the optical beam of the spectrometer in a location such that the light from the sampling optics passes through the transmission cell before being measured by the optical detector. A diffusely reflecting material, such as Spectralon, is placed at the reflective sampling optics interface in order to mimic the bulk scattering properties of tissue. This optical setup allows a similar background to be constructed that uses discrete water pathlengths in transmission to mimic the optical properties of tissue sampled using reflection sampling optics.

The transmission reference sample as shown in FIG. 14 has three different optical pathlengths. When examined by the multipath RMS error metric over the region of 4200–7200 cm$^{-1}$ the magnitude of the residual clearly indicates the presence of multiple pathlengths through generation of a value of approximately 0.11 absorbance units.

Figure 16:
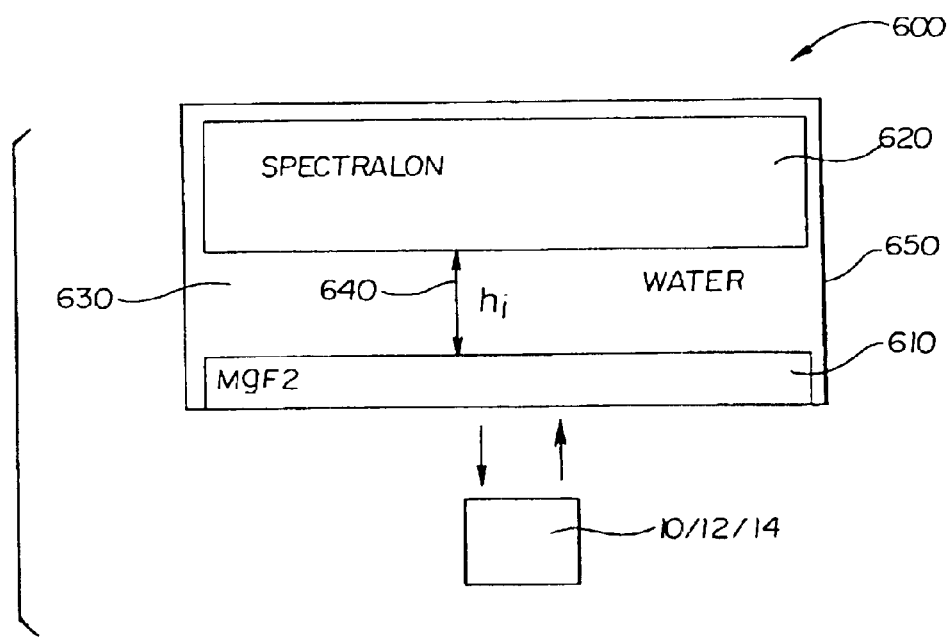
FIG. 16 schematically illustrates a variable height temporal background in accordance with an embodiment of the present invention.

Refer now to FIG. 16, which schematically illustrates a variable height temporal background device 600 in accordance with another embodiment of the present invention. The temporal background device 600 includes an optically transparent layer 610 and a movable diffuse reflector layer 620, such as a Spectralon. A constituent layer 630 such as water is disposed between the optically transparent layer 610 and the diffuse reflector 620. The optically transparent layer 610 may be used to contain the constituent layer 630 or a separate container 650 may be provided for that purpose.

Figure 17:
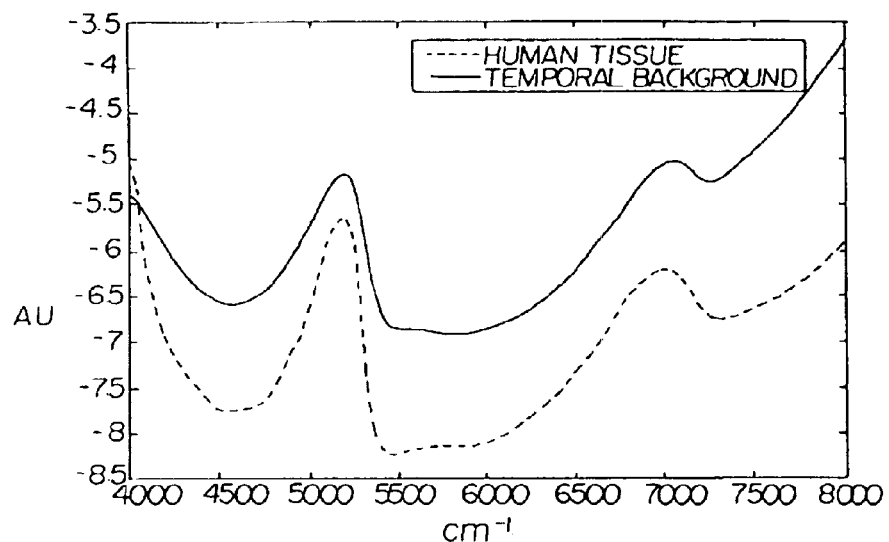
FIG. 17 shows a graph of spectral response demonstrating the spectral match between the tissue sample and the variable height temporal background.

The temporal background device 600 uses a time-weighted sampling technique to produce proper throughput at various pathlengths that match the tissue path distribution. This, in turn, enables the spectral match to tissue. A diffuse reflector 620 (approximately Lambertian high-reflectance material) is used to provide return illumination in the form of reflected light and is translated vertically (as shown by arrow 640 and labeled $h_z$) to achieve a variable water path. The data presented below were generated by varying the height of the Spectralon reflector 620 over the water layer hi through values ranging from 0.1 mm to 0.3 mm. The diameters of the $MgF_2$ window and Spectralon reflector are chosen to match the output area of the sampling optics for a given device. Thus, the reflecting layer 620 is moved to a height corresponding to a given pathlength in the desired distribution, and light is subjected to this pathlength and collected for a time proportional to the weight of the particular path in the distribution. Upon combination of the time-sampled data, a match to the tissue spectrum can be achieved as shown in FIG. 17.

Figure 18:
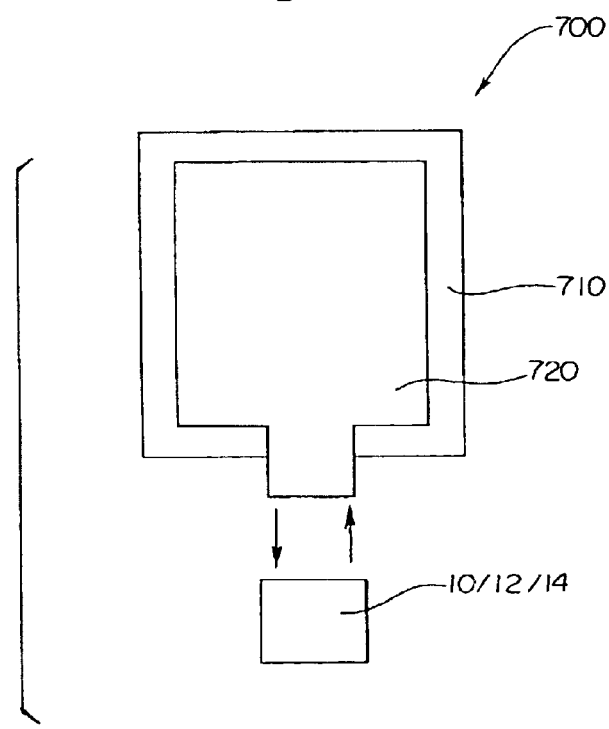
FIG. 18 schematically illustrates a collagen gel matrix background in accordance with an embodiment of the present invention.
Figure 19:
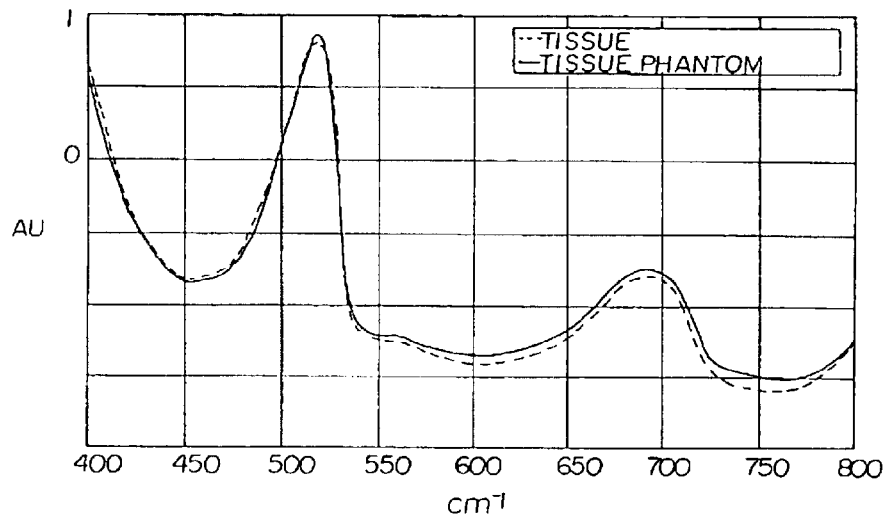
FIG. 19 shows a graph of spectral response demonstrating the spectral match between the tissue sample and the collagen gel matrix background.

Refer now to FIG. 18, which schematically illustrates a collagen gel matrix background device 700 in accordance with an embodiment of the present invention. The collagen gel matrix background device 700 includes a container 710 that is partially optically transparent. A constituent 720 is disposed in the container and comprises a collagen gel matrix. The collagen gel matrix may consist of denatured porcine collagen in a gel state. Reflectance microbeads may be infused into the gel to create a randomized scattering path throughout the volume of the constituent 720. For example, the collagen matrix 720 may be made from 30% porcine gelatin, 0.8% 2 $\mu$m polystyrene beads, and 69.2% water. FIG. 19 shows a graph of spectral response demonstrating the spectral match between the tissue sample spectrum and the collagen gel matrix background spectrum 700. The actual gel thickness presented to the sampling system was 3.0 cm–4.0 cm. As can be seen from FIG. 19, a close match to human tissue can be made if the proper preparation of the collagen gelatin matrix is carried out, which can be accomplished empirically. As one of skill in the art will recognize, the gel matrix can be composed of any substance that enables a optically similar reference sample to be created.

Figure 20:
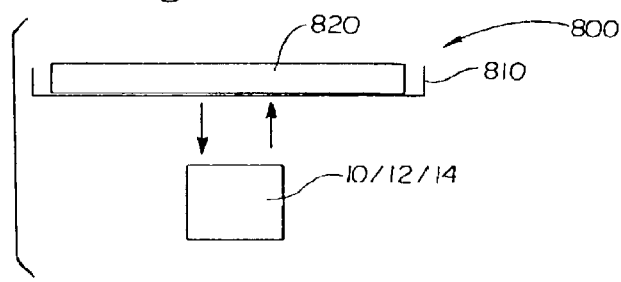
FIG. 20 schematically illustrates an animal tissue (bovine) background in accordance with an embodiment of the present invention.
Figure 21:
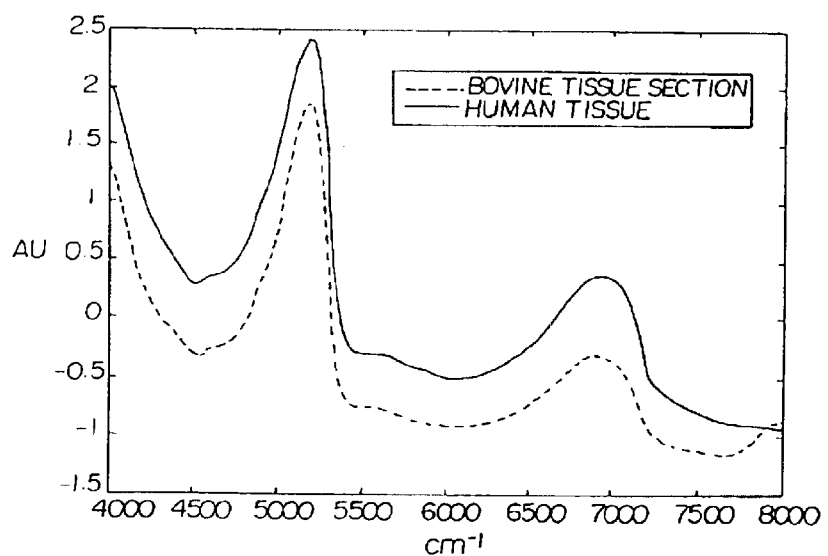
FIG. 21 shows a graph of spectral response demonstrating the spectral match between the tissue sample and the bovine tissue background.

Refer now to FIG. 20, which schematically illustrates an animal based bodily constituent (e.g., bovine tissue) background device 800 in accordance with an embodiment of the present invention. The animal based bodily constituent background 800 includes a container 810 that is at least partially optically transparent and an animal (e.g., bovine, porcine) based bodily constituent 820 disposed therein. The animal based bodily constituent may comprise an animal bodily tissue (e.g., skin), an animal bodily fluid (e.g., blood) or other animal based biological constituent. Through the use of a section of bovine tissue, a relative match to human tissue is readily attained. The bovine tissue section may be doped with analytes in order to simulate various in-vivo concentration levels for humans. Because the spectral features of the bovine tissue section are similar to those found in human tissue, it provides a good formulation of a tissue similar background for use in calibration maintenance. FIG. 21 shows a graph of spectral response demonstrating the spectral match between the tissue sample and the bovine tissue background 800. For the data shown in FIG. 21, 2 cm×4 cm rectangular sections of bovine collagen tissue approximately 1 cm thick were used. The bovine collagen sample comprised a section of cowhide immersed in distilled water to prevent dehydration.

All of the reference sample devices having similar backgrounds discussed above may be used in conjunction with an optical spectrometer, which typically includes, among other components, an illumination source and a collection system. The reference sample is optically coupled (e.g., positioned adjacent) to the illumination source and irradiated with multiple wavelengths of radiation from the illumination source. The collection system is used to collect radiation that is not absorbed by the reference sample. The collected radiation is then used to determine the intensities of the non-absorbed radiation at each of the multiple wavelengths to generate a reference spectrum. A new calibration model can be created or a pre-existing calibration model can be modified based on the reference spectrum to account for instrument and environment variations. Alternatively, the reference spectrum is simply used to alter a spectrum of a test sample to account for instrument and environment variations without altering an existing model.

After the calibration model has been created or modified, a test sample of interest is optically coupled (e.g., positioned adjacent) to the illumination source. The test sample (e.g., human tissue or blood) is irradiated with multiple wavelengths of radiation from the illumination source. Radiation that is not absorbed by the test sample is collected with the collection system. The collected radiation is then used to determine the intensities of the non-absorbed radiation at each of the multiple wavelengths to generate a test spectrum corresponding to the test sample of interest. In one embodiment, the newly created or modified calibration model is used, and an analyte or attribute of the test sample may be calculated based on the test spectrum. Alternatively, the test sample spectrum is modified based on the reference spectrum (i.e., a ratio or difference) and the modified test spectrum is used with an existing model to determine an analyte concentration or attribute.

Note that these steps may be reordered and/or modified without departing from the scope of the present invention. For example, the reference sample may have the same or separate interface with the instrument as that used for the test sample of interest. Also, the reference sample may have multiple components that are simultaneously measured at different locations in the optical path of the spectroscopic instrument. Further, the reference sample may be manually or automatically positioned and measured.

In order to correct for the effects of instrument and environmental variation, the similar background is preferably sampled sufficiently close in time to the sample of interest. The required frequency of sampling for the background is dependent on instrument stability and environmental variations which are being corrected. Preferably, a background measurement is made just prior to measuring the sample of interest which allows the most current instrument state to be determined. In an alternative sampling scheme, the signal-to-noise ratio in the measured background spectrum is improved by taking multiple similar background measurements prior to measuring the sample of interest.

There are several schemes for optimizing the relationship between using multiple background sample measurements (higher signal-to-noise) and using only the background sample measurement made closest in time to the measurement of the sample of interest (most current instrument state). One such scheme is to use multiple, weighted, time-averaged background sample measurements. Multiple background sample measurements are collected over a period of time in order to increase the spectrum's signal-to-noise ratio. Weighted averaging allows those background sample spectra taken closest in time to the sample of interest to more heavily influence the spectral correction.

There are multiple methods for using the spectral measurement of the similar background to correct for instrument and environmental variation. One simple and effective methodology is to ratio the measured spectrum of the sample of interest to the measured spectrum of the similar background sample. This correction methodology removes spectral variation that is common to both the similar background and the sample of interest. This methodology may be used to both establish and maintain a multivariate calibration model, but in some cases, it is desirable to use this methodology only for calibration maintenance.

From the foregoing, it will be apparent to those skilled in the art that the present invention provides devices, systems and methods for establishing and/or maintaining the prediction capability over time of a multivariate calibration model designed for quantitative optical spectroscopic measurement of attributes or analytes in bodily tissues, bodily fluids or other biological samples. The present invention is particularly useful when the spectral absorbance of the attribute or analyte is small relative to the background. The present invention provides an optically similar background reference sample to capture the characteristics of instrument and environmental variation and to reduce the effect of such variation on the measurement capability of the model.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A reference sample for maintaining prediction performance of an optical system used to measure an analyte or attribute in a representative measurement sample, wherein the representative measurement sample comprises a bodily tissue, bodily fluid or other biological sample containing the analyte or attribute and having a dominant absorbing species therein when in vivo, the reference sample comprising the dominant absorbing species contained and disposed such that an optical signal interrogating the reference sample is subjected to diffuse reflection, where the reference sample and the measurement sample absorb light at each of selected wavelengths in a manner to produce similarly shaped spectra over the wavelengths measured, wherein the reference sample has the spectral characteristics of an in vivo sample.

2. A reference sample as in claim 1, wherein the representative measurement sample includes multiple samples from multiple subjects.

3. A reference sample as in claim 2, wherein the reference sample has a spectral similarity ratio, when compared with the representative measurement sample spectra, of 30 or less when evaluated over the selected wavelengths measured.

4. The reference sample of claim 3, wherein the measurement sample is tissue and the selected wavelengths measured is a spectral range of 4,200 $cm^{-1}$ to 7,200 $cm^{-1}$.

5. The reference sample of claim 3, wherein the measurement sample is tissue and the selected wavelengths measured is a spectral range of 4,440 $cm^{-1}$ to 4,800 $cm^{-1}$ and 5,440 $cm^{-1}$ to 6,400 $cm^{-1}$.

6. The reference sample of claim 3, wherein the measurement sample is tissue, the analyte being measured is glucose and the selected wavelengths measured, in wavenumbers ($cm^{-1}$), are selected from the group consisting of: 4196, 4227, 4273, 4281, 4304, 4320, 4335, 4366, 4389, 4436, 4451, 4459, 4497, 4528, 4559, 4613, 4690, 4775, 4829, 4860, 4883, 4922, 5014, 5091, 5176, 5230, 5269, 5299, 5315, 5338, 5369, 5392, 5454, 5469, 5477, 5515, 5585, 5623, 5662, 5701, 5731, 5755, 5785, 5809, 5839, 5893, 5924, 5947, 6001, 6094, 6163, 6187, 6287, 6318, 6349, 6449, 6472, 6557, 6595, 6673, 6696, 6935, 6973, 7004, 7043, 7066, 7205, and combinations thereof.

7. A reference sample as in claim 2, wherein the reference sample has a spectral similarity ratio, when compared with the representative measurement sample spectra, of 10 or less when evaluated over the selected wavelengths measured.

8. A reference sample as in claim 2, wherein the reference sample has a spectral similarity ratio, when compared with the representative measurement sample spectra, of 1 or less when evaluated over the selected wavelengths measured.

9. The reference sample of claim 8, wherein the measurement sample is tissue and the selected wavelengths measured is a spectral range of 4,200 $cm^{-1}$ to 7,200 $cm^{-1}$.

10. The reference sample of claim 8, wherein the measurement sample is tissue and the selected wavelengths measured is a spectral range of 4,440 $cm^{-1}$ to 4,800 $cm^{-1}$ and 5,440 $cm^{-1}$ to 6,400 $cm^{-1}$.

11. The reference sample of claim 8, wherein die measurement sample is tissue, the analyte being measured is glucose and the selected wavelengths measured, in wavenumbers ($cm^{-1}$), are selected from the group consisting of: 4196, 4227, 4273, 4281, 4304, 4320, 4335, 4366, 4389, 4436, 4451, 4459, 4497, 4528, 4559, 4613, 4690, 4775, 4829, 4860, 4383, 4922, 5014, 5091, 5176, 5230, 5269, 5299, 5315, 5338, 5369, 5392, 5454, 5469, 5477, 5515, 5585, 5623, 5662, 5701, 5731, 5755, 5785, 5809, 5839, 5893, 5924, 5947, 6001, 6094, 6163, 6187, 6287, 6318, 6349, 6449, 6472, 6557, 6595, 6673, 6696, 6935, 6973, 7004, 7043, 7066, 7205, and combinations thereof.

12. A reference sample as in claim 2, wherein the reference sample has a regression weighted spectral similarity ratio, when compared to the representative measurement sample spectra, of 30 or less.

13. A reference sample as in claim 2, wherein the reference sample has a regression weighted spectral similarity ratio, when compared to the representative measurement sample spectra, of 10 or less.

14. A reference sample as in claim 2, wherein the reference sample has a regression weighted spectral similarity ratio, when compared to the representative measurement sample spectra, of 1 or less.

15. The reference sample of claim 1, wherein the measurement sample is tissue and the selected wavelengths measured is a spectral range of 4,200 $cm^{-1}$ to 7,200 $cm^{-1}$.

16. The reference sample of claim 1, wherein the measurement sample is tissue and the selected wavelengths measured is a spectral range of 4,440 $cm^{-1}$ to 4,800 $cm^{-1}$ and 5,440 $cm^{-1}$ to 6,400 $cm^{-1}$.

17. The reference sample of claim 1, wherein the measurement sample is tissue, the analyte being measured is glucose and the selected wavelengths measured, in wavenumbers ($cm^{-1}$), are selected from the group consisting of: 4196, 4227, 4273, 4281, 4304, 4320, 4335, 4366, 4389, 4436, 4451, 4459, 4497, 4528, 4559, 4613, 4690, 4775, 4829, 4860, 4883, 4922, 5014, 5091, 5176, 5230, 5269, 5299, 5315, 5338, 5369, 5392, 5454, 5469, 5477, 5515, 5585, 5623, 5662, 5701, 5731, 5755, 5785, 5809, 5839, 5893, 5924, 5947, 6001, 6094, 6163, 6187, 6287, 6318, 6349, 6449, 6472, 6557, 6595, 6673, 6696, 6935, 6973, 7004, 7043, 7066, 7205, and combinations thereof.

18. A reference sample as in claim 1, wherein the representative measurement sample is from a single subject.

19. A reference sample as in claim 18, wherein the reference sample has a spectral similarity ratio, when compared with the representative measurement sample spectra, of 1500 or less when evaluated over the selected wavelengths measured.

20. The reference sample of claim 19, wherein the measurement sample is tissue and the selected wavelengths measured is a spectral range of 4,200 $cm^{-1}$ to 7,200 $cm^{-1}$.

21. The reference sample of claim 19, wherein the measurement sample is tissue and the selected wavelengths measured is a spectral range of 4,440 $cm_{31\ 1}$ to 4,800 $cm^{-1}$ and 5,440 $cm^{-1}$ to 6,400 $cm^{-1}$.

22. The reference sample of claim 19, wherein the measurement sample is tissue, the analyte being measured is glucose and the selected wavelengths measured, in wavenumbers ($cm^{-1}$), are selected from the group consisting of: 4196, 4227, 4273, 4281, 4304, 4320, 4335, 4366, 4389, 4436, 4451, 4459, 4497, 4528, 4559, 4613, 4690, 4775, 4829, 4860, 4883, 4922, 5014, 5091, 5176, 5230, 5269, 5299, 5315, 5338, 5369, 5392, 5454, 5469, 5477, 5515, 5585, 5623, 5662, 5701, 5731, 5755, 5785, 5809, 5839, 5893, 5924, 5947, 6001, 6094, 6163, 6187, 6287, 6318, 6349, 6449, 6472, 6557, 6595, 6673, 6696, 6935, 6973, 7004, 7043, 7066, 7205, and combinations thereof.

23. A reference sample as in claim 18, wherein the reference sample has a spectral similarity ratio, when compared with the representative measurement sample spectra, of 1000 or less when evaluated over the selected wavelengths measured.

24. The reference sample of claim 23, wherein the measurement sample is tissue and the selected wavelengths measured is a spectral range of 4,200 $cm^{-1}$ to 7,200 $cm^{-1}$.

25. The reference sample of claim 23, wherein the measurement sample is tissue and the selected wavelengths measured is a spectral range of 4,440 $cm^{-1}$ to 4,800 $cm^{-1}$ and 5,440 $cm^{-1}$ to 6,400 $cm^{-1}$.

26. The reference sample of claim 23, wherein the measurement sample is tissue, the analye being measured is glucose and the selected wavelengths measured, in wavenumbers ($cm^{-1}$), are selected from the group consisting of: 4196, 4227, 4273, 4281, 4304, 4320, 4335, 4366, 4389, 4436, 4451, 4459, 4497, 4528, 4559, 4613, 4690, 4775, 4829, 4860, 4883, 4922, 5014, 5091, 5176, 5230, 5269, 5299, 5315, 5338, 5369, 5392, 5454, 5469, 5477, 5515, 5585, 5623, 5662, 5701, 5731, 5755, 5785, 5809, 5839, 5893, 5924, 5947, 6001, 6094, 6163, 6187, 6287, 6318, 6349, 6449, 6472, 6557, 6595, 6673, 6696, 6935, 6973, 7004, 7043, 7066, 7205, and combinations thereof.

27. A reference sample as in claim 18, wherein the reference sample has a spectral similarity ratio, when compared with the representative measurement sample spectra, of 1 or less when evaluated over the selected wavelengths measured.

28. The reference sample of claim 27, wherein the measurement sample is tissue and the selected wavelengths measured is a spectral range of 4,200 $cm^{-1}$ to 7,200 $cm^{-1}$.

29. The reference sample of claim 27, wherein the measurement sample is tissue and the selected wavelengths measured is a spectral range of 4,440 $cm^{-1}$ to 4,800 $cm^{-1}$ and 5,440 $cm^{-1}$ to 6,400 $cm^{-1}$.

30. The reference sample of claim 27 wherein the measurement sample is tissue, the analyte being measured is glucose and the selected wavelengths measured, in wavenumbers ($cm^{-1}$), are selected from the group consisting of: 4196, 4227, 4273, 4281, 4304, 4320, 4335, 4366, 4389, 4436, 4451, 4459, 4497, 4528, 4559, 4613, 4690, 4775, 4829, 4860, 4883, 4922, 5014, 5091, 5176, 5230, 5269, 5299, 5315, 5338, 5369, 5392, 5454, 5469, 5477, 5515, 5585, 5623, 5662, 5701, 5731, 5755, 5785, 5809, 5839, 5893, 5924, 5947, 6001, 6094, 6163, 6187, 6287, 6318, 6349, 6449, 6472, 6557, 6595, 6673, 6696, 6935, 6973, 7004, 7043, 7066, 7205, and combinations thereof.

31. A reference sample as in claim 18, wherein the reference sample has a regression weighted spectral similarity ratio, when compared to the representative measurement sample spectra, of 4500 or less.

32. A reference sample as in claim 18, wherein the reference sample has a regression weighted spectral similarity ratio, when compared to the representative measurement sample spectra, of 1500 or less.

33. A reference sample as in claim 18, wherein the reference sample has a regression weighted spectral similarity ratio, when compared to the representative measurement sample spectra, of 1 or less.

34. A reference sample for maintaining prediction performance of an optical system used to measure an analyte or attribute in a representative measurement sample, the reference sample including a dominant absorbing species housed in a structure defining a plurality of dispersive optical interfaces, the dominant absorbing species corresponding to a dominant absorbing material present in the representative measurement sample when in vivo, wherein the representative measurement sample comprise a bodily tissue, bodily fluid or other biological sample containing the analyte or attribute, where the reference sample simulates the optical interaction between the measurement sample and the optical system.

35. A reference sample as in claim 34, wherein the reference sample has a spatial similarity, expressed in terms of standard deviation, of 0.079 or less.

36. A reference sample as in claim 34, wherein the reference sample has a spatial similarity, expressed in terms of standard deviation, of 0.052 or less.

37. A reference sample as in claim 34, wherein the reference sample has a spatial similarity, expressed in terms of standard deviation, of approximately 0.0.

38. A reference sample as in claim 34, wherein the reference sample has an angular similarity, expressed in terms of standard deviation, of 0.051 or less.

39. A reference sample as in claim 34, wherein the reference sample has an angular similarity, expressed in terms of standard deviation, of 0.036 or less.

40. A reference sample as in claim 34, wherein the reference sample has an angular similarity, expressed in terms of standard deviation, of approximately 0.0.

41. A reference sample for maintaining prediction performance of an optical system to measure an analyte or attribute in a representative measurement sample, wherein the representative measurement sample comprises a bodily tissue, bodily fluid or other biological sample containing the analyte or attribute as well as a dominant absorbing species present when the representative measurement sample is in vivo, where the reference sample has the same primary optical absorber as the measurement sample, wherein the reference sample has the spectral characteristics of an in vivo sample, the dominant absorbing species being the primary optical absorber, the dominant absorbing species being contained in a housing allowing optical interrogation thereof.

42. A reference sample as in claim 41, wherein the representative measurement sample contains first and second primary constituents, and wherein the reference sample contains the same first and second primary constituents.

43. A reference sample as in claim 42, wherein the second primary constituent comprises protein.

44. A reference sample as in claim 42, wherein the second primary constituent comprises lipid.

45. A reference sample as in claim 42, wherein the second primary constituent comprises a organic polymer.

46. A reference sample as in claim 41, wherein the measurement sample is tissue and the portion of the reference sample that is optically sampled contains less than 80% water by volume.

47. A reference sample for maintaining prediction performance of an optical system used to measure an analyte or attribute in a representative measurement sample, wherein the representative measurement sample comprises a bodily tissue, bodily fluid or other biological sample containing the analyte or attribute, with the reference sample including a structure having one or more optically interactive surfaces and producing a non-stepwise reference spectrum that is optically similar to the representative measurement sample, both the reference sample and the representative measurement sample having a primary optical absorber corresponding to a dominant in vivo optical absorber for the representative measurement sample.

48. A reference sample as in claim 47, wherein the reference sample includes:
    an optically transparent layer;
    a diffusing layer; and
    a constituent layer disposed between the optically transparent layer and the diffusing layer.

49. A reference sample as in claim 48, wherein the representative measurement sample contains a primary constituent, and wherein the constituent layer contains the same primary constituent.

50. A reference sample as in claim 49, wherein the constituent layer contains water.

51. A reference sample as in claim 49, wherein the constituent layer contains protein.

52. A reference sample as in claim 49, wherein the constituent layer contains lipid.

53. A reference sample as in claim 48, wherein the diffusing layer is cone shaped.

54. A reference sample as in claim 48, wherein the optically transparent layer, the constituent layer, and the diffusing layer are cone shaped.

55. A reference sample as in claim 48, wherein the diffusing layer is non-planar.

56. A reference sample as in claim 48, wherein the optically transparent layer is flat.

57. A reference sample as in claim 47, wherein the reference sample includes:
    a container that is at least partially optically transparent; and
    a scattering solution in the container.

58. A reference sample as in claim 57, wherein the reference sample further includes a stirring mechanism for stirring the scattering solution.

59. A reference sample as in claim 57, wherein the scattering solution comprises reflective beads disposed in a constituent.

60. A reference sample as in claim 47, wherein the reference sample includes:
    a first optical splitting layer;
    a reflective layer; and
    a first constituent layer disposed between the first optical splitting layer and the reflective layer.

61. A reference sample as in claim 60, wherein the representative measurement sample contains a primary constituent, and wherein the first constituent layer contains the same primary constituent.

62. A reference sample as in claim 61, wherein the constituent layer contains water.

63. A reference sample as in claim 60, wherein the reference sample further includes:
    a second optical splitting layer; and
    a second constituent layer disposed between the first optical splitting layer and the second optical splitting layer.

64. A reference sample as in claim 47, wherein the reference sample includes:
    a container that is at least partially optically transparent;
    a constituent disposed in the container; and
    a spacer disposed in the container.

65. A reference sample as in claim 64, wherein the representative measurement sample contains a primary constituent, and wherein the constituent disposed in the container comprises the same primary constituent.

66. A reference sample as in claim 65, wherein the constituent disposed in the container comprises water.

67. A reference sample as in claim 64, wherein multiple spacers are disposed in the container.

68. A reference sample as in claim 47, wherein the reference sample includes:
    an optically transparent layer;
    a diffuse reflective layer disposed a distance from the optically transparent layer; and
    a constituent layer disposed between the optically transparent layer and the diffuse reflective layer.

69. A reference sample as in claim 68, wherein the representative measurement sample contains a primary constituent, and wherein the constituent layer comprises the same primary constituent.

70. A reference sample as in claim 68, wherein the constituent layer comprises water.

71. A reference layer as in claim 68, wherein the diffuse reflective layer is movable relative to the optically transparent layer to change the distance therebetween.

72. A reference sample as in claim 47, wherein the reference sample includes:
    a animal based bodily constituent.

73. A reference sample as in claim 72, wherein the animal based bodily constituent comprises animal bodily tissue.

74. A reference sample as in claim 72, wherein the animal based bodily constituent comprises animal bodily fluid.

75. A reference sample as in claim 47, wherein the reference sample includes:
    a gel matrix;
    scattering media; and
    water.

76. A reference sample as in claim 75, wherein the gel matrix is placed in direct contact with the optical sampling device.

77. A reference sample as in claim 75, wherein the gel matrix is contained in a container that enables optical sampling.

78. A reference sample for maintaining prediction performance or an optical system used to measure an analyte or attribute in a test sample of interest, wherein the test sample comprises a bodily tissue, bodily fluid or other biological sample containing the analyte or attribute, with the reference sample producing a reference sample spectrum that is similar to the test sample spectrum, the reference sample including a transmissive optical interface and an optical sampling compartment, the optical sampling compartment containing water and a diffusely reflective or scattering media and including structure such that an optical signal passing through the transmissive optical interface encounters reflective surfaces at various path lengths from the optical interface.

79. A reference sample as in claim 78, wherein the reference sample spectrum has a spectral similarity ratio, when compared to a representative measurement sample spectra, of 30 or less.

80. A reference sample as in claim 78, wherein the reference sample spectrum has a regression weighted spectral similarity ratio, when compared to a representative measurement sample spectra, of 30 or less.

81. A reference sample as in claim 78, wherein the reference sample has a spatial similarity, expressed in terms of standard deviation, of 0.079 or less.

82. A reference sample as in claim 78, wherein the reference sample has an angular similarity, expressed in terms of standard deviation, of 0.051 or less.

83. A reference device for use with an optical system to maintain prediction performance of the optical system for a constituent of a representative measurement sample, the reference device comprising:

a reference material having a first optical similarity to the representative measurement sample; and a structure for containing the reference material in a geometric configuration adapted to give the reference device a second optical similarity to the representative measurement sample;

wherein the second optical similarity is greater than the first optical similarity.

84. The reference device of claim 83, wherein the structure includes an optical interface allowing light to enter the reference device and interact with the reference material.

85. The reference device of claim 84, wherein the structure includes a diffusing cone.

86. The reference device of claim 83, wherein the structure provides a geometric configuration such that light entering the reference device may interact with the reference material through several different pathlengths.

* * * * *

UNITED STATES PATENT AND TRADEMARK OFFICE
CERTIFICATE OF CORRECTION

PATENT NO. : 6,983,176 B2  
APPLICATION NO. : 09/832608  
DATED : January 3, 2006  
INVENTOR(S) : Craig Gardner et al.

It is certified that error appears in the above-identified patent and that said Letters Patent is hereby corrected as shown below:

Column 13,  
Lines 52-58, delete Equation 7, and insert $$\frac{T_{s+\Delta}^{A}(\bar{v}_i)}{T_{h+\Delta}^{A}(\bar{v}_i)} = \frac{\int_0^\infty \sigma(\bar{v}-\bar{v}_i)e^{-\kappa_I(\bar{v})l_I}e^{-\kappa_s(\bar{v})l_s}e^{-\kappa_w(\bar{v})l_w}e^{-\kappa_v(\bar{v})l_v}e^{-\kappa_\Delta(\bar{v})l_\Delta}}{\int_0^\infty \sigma(\bar{v}-\bar{v}_i)e^{-\kappa_I(\bar{v})l_I}e^{-\kappa_v(\bar{v})l_v}e^{-\kappa_\Delta(\bar{v})l_\Delta}}$$

Column 30,  
Line 28, delete "die", and insert -- the --.  
Line 34, delete "4383", and insert -- 4883 --.

Column 31,  
Line 43, delete "analye", and insert -- analyte --.

Signed and Sealed this

Twenty-seventh Day of June, 2006

JON W. DUDAS  
*Director of the United States Patent and Trademark Office*